(12) United States Patent
Kovarik

(10) Patent No.: US 11,969,445 B2
(45) Date of Patent: Apr. 30, 2024

(54) PROBIOTIC COMPOSITION AND METHOD FOR CONTROLLING EXCESS WEIGHT, OBESITY, NAFLD AND NASH

(71) Applicant: Seed Health, Inc., Venice, CA (US)

(72) Inventor: Joseph E. Kovarik, Englewood, CO (US)

(73) Assignee: Seed Health, Inc., Venice, CA (US)

( * ) Notice: Subject to any disclaimer, the term of this patent is extended or adjusted under 35 U.S.C. 154(b) by 0 days.

(21) Appl. No.: 18/232,980

(22) Filed: Aug. 11, 2023

(65) Prior Publication Data

US 2024/0016856 A1  Jan. 18, 2024

Related U.S. Application Data

(63) Continuation-in-part of application No. 18/232,433, filed on Aug. 10, 2023, which is a continuation-in-part of application No. 18/143,399, filed on May 4, 2023, which is a continuation of application No. 17/893,384, filed on Aug. 23, 2022, which is a continuation-in-part of application No. 17/694,775, filed on Mar. 15, 2022, which is a continuation-in-part of application No. 17/023,736, filed on Sep. 17, 2020, now Pat. No. 11,419,903, which is a continuation-in-part of application No. 17/011,175, filed on Sep. 3, 2020, now Pat. No. 11,273,187, which is a continuation-in-part of application No. 16/722,117, filed on Dec. 20, 2019, now Pat. No. 10,842,834, which is a continuation-in-part of application No. 16/229,252, filed on Dec. 21, 2018, now Pat. No. 10,512,661, which is a continuation-in-part of application No. 15/392,173, filed on Dec. 28, 2016, now Pat. No. 10,245,288, application No. 18/232,980 is a continuation-in-part of application No. 18/130,946, filed on Apr. 5, 2023, now Pat. No. 11,833,177, which is a continuation-in-part of application No. 18/178,847, filed on Mar. 28, 2023, now Pat. No. 11,839,632, which is a continuation-in-part of application No. 18/087,545, filed on Dec. 22, 2022, now Pat. No. 11,826,388, which is a continuation-in-part of application No. 17/854,422, filed on Jun. 30, 2022, now Pat. No. 11,672,835, which is a continuation-in-part of application No. 17/848,759, filed on Jun. 24, 2022, now Pat. No. 11,642,382, which is a continuation-in-part of application No. 17/835,204, filed on Jun. 8, 2022, now Pat. No. 11,529,379, which is a continuation-in-part of application No. 17/567,295, filed on Jan. 3, 2022, which is a continuation-in-part of application No. 17/337,600, filed on Jun. 3, 2021, now Pat. No. 11,213,552, which is a continuation-in-part of application No. 17/027,953, filed on Sep. 22, 2020, now Pat. No. 11,026,982, which is a continuation-in-part of application No. 16/917,096, filed on Jun. 30, 2020, now Pat. No. 10,940,169, which is a continuation-in-part of application No. 16/782,364, filed on Feb. 5, 2020, now Pat. No. 10,835,560, which is a continuation-in-part of application No. 16/423,375, filed on May 28, 2019, now Pat. No. 10,555,976, which is a continuation of application No. 16/160,336, filed on Oct. 15, 2018, now Pat. No. 10,314,866, which is a continuation of application No. 15/403,823, filed on Jan. 11, 2017, now Pat. No. 10,111,913, application No. 18/232,980 is a (Continued)

(51) Int. Cl.
| | | |
|---|---|---|
| A61K 35/74 | (2015.01) | |
| A61K 31/58 | (2006.01) | |
| A61K 31/715 | (2006.01) | |
| A61K 35/00 | (2006.01) | |
| A61K 38/17 | (2006.01) | |

(52) U.S. Cl.
CPC .............. *A61K 35/74* (2013.01); *A61K 31/58* (2013.01); *A61K 31/715* (2013.01); *A61K 38/1709* (2013.01); *A61K 38/1758* (2013.01); *A61K 2035/11* (2013.01)

(58) Field of Classification Search
None
See application file for complete search history.

(56) References Cited

U.S. PATENT DOCUMENTS

| | | |
|---|---|---|
| 1,492,600 A | 5/1924 | Laskey |
| 3,178,341 A | 4/1965 | Hamill et al. |

(Continued)

FOREIGN PATENT DOCUMENTS

| | | |
|---|---|---|
| DE | 4412190 | 10/1995 |
| EP | 410696 | 1/1991 |

(Continued)

OTHER PUBLICATIONS

U.S. Appl. No. 17/854,389, filed Jun. 30, 2022, Kovarik.

(Continued)

*Primary Examiner* — Brian Gangle
(74) *Attorney, Agent, or Firm* — Sheridan Ross P.C.

(57) ABSTRACT

A method and system for modulating an individual's microbiome in a manner such that individuals who are overweight, obese and/or suffer from cardiometabolic diseases and/or inflammatory bowel diseases are able to reduce the incidence of chronic conditions and diseases associated therewith. Certain embodiments are directed to a method and bacterial formulations for reducing the likelihood of developing NAFLD and NASH.

18 Claims, 1 Drawing Sheet

Related U.S. Application Data continuation-in-part of application No. 18/103,768, filed on Jan. 31, 2023, now Pat. No. 11,844,720, which is a continuation-in-part of application No. 17/738,771, filed on May 6, 2022, which is a continuation-in-part of application No. 16/904,056, filed on Jun. 17, 2020, now Pat. No. 11,523,934, which is a continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, application No. 18/232,980 is a continuation-in-part of application No. 17/836,079, filed on Jun. 9, 2022, which is a continuation-in-part of application No. 16/884,772, filed on May 27, 2020, now Pat. No. 11,357,722, which is a continuation-in-part of application No. 16/136,950, filed on Sep. 20, 2018, now Pat. No. 10,668,014, which is a continuation of application No. 15/385,278, filed on Dec. 20, 2016, now Pat. No. 10,085,938, application No. 18/232,980 is a continuation-in-part of application No. 17/543,992, filed on Dec. 7, 2021, which is a continuation-in-part of application No. 16/804,361, filed on Feb. 28, 2020, now Pat. No. 11,191,665, which is a continuation-in-part of application No. 16/020,433, filed on Jun. 27, 2018, now Pat. No. 10,583,033, which is a continuation-in-part of application No. 15/342,642, filed on Nov. 3, 2016, now Pat. No. 10,010,568, application No. 18/232,980 is a continuation-in-part of application No. 16/776,861, filed on Jan. 30, 2020, now Pat. No. 10,864,109, which is a continuation of application No. 16/142,171, filed on Sep. 26, 2018, now Pat. No. 10,548,761, which is a continuation-in-part of application No. 15/395,419, filed on Dec. 30, 2016, now Pat. No. 10,086,018, application No. 18/232,980 is a continuation-in-part of application No. 16/426,346, filed on May 30, 2019 now Pat. No. 10,716,815, which is a continuation of application No. 15/639,767, filed on Jun. 30, 2017, now Pat. No. 10,314,865, which is a continuation-in-part of application No. 15/437,976, filed on Feb. 21, 2017, now Pat. No. 9,730,967, which is a continuation-in-part of application No. 15/228,454, filed on Aug. 4, 2016, now Pat. No. 9,585,920, which is a continuation-in-part of application No. 14/954,074, filed on Nov. 30, 2015, now Pat. No. 9,457,077, application No. 18/232,980 is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 18/232,980 is a continuation-in-part of application No. 16/037,053, filed on Jul. 17, 2018, now abandoned, and a continuation-in-part of application No. 14/752,192, filed on Jun. 26, 2015, now Pat. No. 9,549,842.

(60) Provisional application No. 62/275,341, filed on Jan. 6, 2016, provisional application No. 62/296,186, filed on Feb. 17, 2016, provisional application No. 62/387,405, filed on Dec. 24, 2015, provisional application No. 62/387,404, filed on Dec. 24, 2015, provisional application No. 62/260,906, filed on Nov. 30, 2015, provisional application No. 62/274,550, filed on Jan. 4, 2016, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013.

(56) References Cited

U.S. PATENT DOCUMENTS

| | | |
|---|---|---|
| 3,640,741 A | 2/1972 | Etes |
| 3,832,460 A | 8/1974 | Kosti |
| 3,996,934 A | 12/1976 | Zaffaroni |
| 4,136,145 A | 1/1979 | Fuchs et al. |
| 4,136,162 A | 1/1979 | Fuchs et al. |
| 4,163,777 A | 8/1979 | Mitra |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,568,639 A | 2/1986 | Lew |
| 4,572,832 A | 2/1986 | Kigasawa et al. |
| 4,668,232 A | 5/1987 | Cordes et al. |
| 4,687,841 A | 8/1987 | Spilburg et al. |
| 4,713,243 A | 12/1987 | Schiraldi et al. |
| 4,715,369 A | 12/1987 | Susuki et al. |
| 4,720,486 A | 1/1988 | Spilburg et al. |
| 4,740,365 A | 4/1988 | Yukimatsu et al. |
| 4,765,983 A | 8/1988 | Takayanagi et al. |
| 4,830,008 A | 5/1989 | Meer |
| 4,849,246 A | 7/1989 | Schmidt |
| 4,867,970 A | 9/1989 | Newsham et al. |
| 4,889,720 A | 12/1989 | Konishi |
| 4,894,232 A | 1/1990 | Reul et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,995,555 A | 2/1991 | Woodruff |
| 5,002,970 A | 3/1991 | Eby, III |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,158,789 A | 10/1992 | DuRoss |
| 5,166,233 A | 11/1992 | Kuroya et al. |
| 5,190,053 A | 3/1993 | Meer |
| 5,192,802 A | 3/1993 | Rencher |
| 5,196,202 A | 3/1993 | Konishi |
| 5,277,877 A | 1/1994 | Jeffrey et al. |
| 5,284,161 A | 2/1994 | Karell |
| 5,298,258 A | 3/1994 | Akemi et al. |
| 5,314,915 A | 5/1994 | Rencher |
| 5,332,576 A | 7/1994 | Mantelle |
| 5,462,749 A | 10/1995 | Rencher |
| 5,465,734 A | 11/1995 | Alvarez et al. |
| 5,466,465 A | 11/1995 | Royds et al. |
| 5,505,956 A | 4/1996 | Kim et al. |
| 5,518,733 A | 5/1996 | Lamothe et al. |
| 5,578,315 A | 11/1996 | Chien et al. |
| 5,585,098 A | 12/1996 | Coleman |
| 5,614,501 A | 3/1997 | Richards |
| 5,629,003 A | 5/1997 | Horstmann et al. |
| 5,643,603 A | 7/1997 | Bottenberg et al. |
| 5,700,478 A | 12/1997 | Biegajski et al. |
| 5,713,852 A | 2/1998 | Anthony et al. |
| 5,718,702 A | 2/1998 | Edwards |
| 5,719,196 A | 2/1998 | Uhari et al. |
| 5,792,067 A | 8/1998 | Karell |
| 5,800,832 A | 9/1998 | Tapolsky et al. |
| 5,804,211 A | 9/1998 | Robertson et al. |
| 5,843,021 A | 12/1998 | Edwards et al. |

(56) References Cited

U.S. PATENT DOCUMENTS

| | | |
|---|---|---|
| 5,855,872 A | 1/1999 | Libin |
| 5,876,995 A | 3/1999 | Bryan |
| 5,895,804 A | 4/1999 | Lee et al. |
| 5,900,245 A | 5/1999 | Sawhney et al. |
| 5,948,430 A | 9/1999 | Zerbe et al. |
| 5,988,171 A | 11/1999 | Sohn et al. |
| 6,054,143 A | 4/2000 | Jones |
| 6,072,100 A | 6/2000 | Mooney et al. |
| 6,139,861 A | 10/2000 | Friedman |
| 6,161,541 A | 12/2000 | Woodson |
| 6,174,546 B1 | 1/2001 | Therriault et al. |
| 6,210,699 B1 | 4/2001 | Acharya et al. |
| 6,250,307 B1 | 6/2001 | Conrad et al. |
| 6,284,235 B1 | 9/2001 | Foreman et al. |
| 6,287,610 B1 | 9/2001 | Bowling et al. |
| 6,352,711 B1 | 3/2002 | Campbell |
| 6,375,963 B1 | 4/2002 | Repka et al. |
| 6,390,096 B1 | 5/2002 | Conrad et al. |
| 6,431,174 B1 | 8/2002 | Knudson et al. |
| 6,432,986 B2 | 8/2002 | Levin |
| 6,439,238 B1 | 8/2002 | Brenzel et al. |
| 6,453,905 B1 | 9/2002 | Conrad et al. |
| 6,458,380 B1 | 10/2002 | Leaderman |
| 6,458,777 B1 | 10/2002 | Sonis et al. |
| 6,467,485 B1 | 10/2002 | Schmidt |
| 6,502,574 B2 | 1/2003 | Stevens et al. |
| 6,509,028 B2 | 1/2003 | Williams et al. |
| 6,523,542 B2 | 2/2003 | Knudson et al. |
| 6,552,024 B1 | 4/2003 | Chen et al. |
| 6,555,125 B2 | 4/2003 | Campbell |
| 6,569,474 B2 | 5/2003 | Clayton et al. |
| 6,578,580 B2 | 6/2003 | Conrad et al. |
| 6,585,997 B2 | 7/2003 | Moro et al. |
| 6,599,883 B1 | 7/2003 | Romeo et al. |
| 6,620,846 B1 | 9/2003 | Jonn et al. |
| 6,713,463 B2 | 3/2004 | Sonis et al. |
| 6,722,577 B2 | 4/2004 | Dobyns, III |
| 6,726,920 B1 | 4/2004 | Theeuwes et al. |
| 6,734,157 B2 | 5/2004 | Radwanski et al. |
| 6,748,951 B1 | 6/2004 | Schmidt |
| 6,794,318 B2 | 9/2004 | Anderson et al. |
| 6,803,420 B2 | 10/2004 | Cleary et al. |
| 6,916,480 B2 | 7/2005 | Anderson et al. |
| 6,919,373 B1 | 7/2005 | Lam et al. |
| 6,923,981 B2 | 8/2005 | Leung et al. |
| 7,001,609 B1 | 2/2006 | Matson et al. |
| 7,067,116 B1 | 6/2006 | Bess et al. |
| 7,087,249 B2 | 8/2006 | Burrell et al. |
| 7,097,853 B1 | 8/2006 | Garbe et al. |
| 7,122,198 B1 | 10/2006 | Singh et al. |
| 7,138,135 B2 | 11/2006 | Chen et al. |
| 7,143,709 B2 | 12/2006 | Brennan et al. |
| 7,146,981 B2 | 12/2006 | Knudson et al. |
| 7,267,975 B2 | 9/2007 | Strobel et al. |
| 7,276,246 B2 | 10/2007 | Zhang |
| 7,287,646 B2 | 10/2007 | Gierskcky |
| 7,306,812 B2 | 12/2007 | Zhang |
| 7,332,230 B1 | 2/2008 | Krumme |
| 7,353,194 B1 | 4/2008 | Kerker et al. |
| 7,357,891 B2 | 4/2008 | Yang et al. |
| 7,425,292 B2 | 9/2008 | Yang et al. |
| 7,441,559 B2 | 10/2008 | Nelson et al. |
| 7,470,397 B2 | 12/2008 | Meathrel et al. |
| 7,500,484 B2 | 3/2009 | Nelson et al. |
| 7,540,432 B2 | 6/2009 | Majerowski et al. |
| 7,566,310 B2 | 7/2009 | Badr et al. |
| 7,575,739 B2 | 8/2009 | Tamarkin et al. |
| 7,579,019 B2 | 8/2009 | Tapolsky et al. |
| 7,579,078 B2 | 8/2009 | Hartmann et al. |
| 7,615,235 B2 | 11/2009 | Rademacher et al. |
| 7,632,525 B2 | 12/2009 | Dodds et al. |
| 7,645,803 B2 | 1/2010 | Tamarkin et al. |
| 7,648,712 B2 | 1/2010 | Bess et al. |
| 7,650,848 B2 | 1/2010 | Brennan et al. |
| 7,666,502 B2 | 2/2010 | Magill et al. |
| 7,669,603 B2 | 3/2010 | Knudson et al. |
| 7,686,021 B2 | 3/2010 | Knudson et al. |
| 7,704,518 B2 | 4/2010 | Tamarkin et al. |
| 7,727,466 B2 | 6/2010 | Meathrel et al. |
| 7,799,337 B2 | 9/2010 | Levin |
| 7,820,145 B2 | 10/2010 | Tamarkin et al. |
| 7,820,420 B2 | 10/2010 | Whitlock |
| 7,824,588 B2 | 11/2010 | Yang et al. |
| 7,824,704 B2 | 11/2010 | Anderson et al. |
| 7,845,356 B2 | 12/2010 | Paraschac et al. |
| 7,862,808 B2 | 1/2011 | Isolauri et al. |
| 7,901,925 B2 | 3/2011 | Bojrab |
| 7,906,140 B2 | 3/2011 | Bromley et al. |
| 7,937,159 B2 | 5/2011 | Lima et al. |
| 7,984,714 B2 | 7/2011 | Hausmann et al. |
| 7,992,566 B2 | 8/2011 | Pflueger et al. |
| 7,997,266 B2 | 8/2011 | Frazier et al. |
| 8,030,457 B2 | 10/2011 | Jackson et al. |
| 8,034,601 B2 | 10/2011 | Boileau et al. |
| 8,034,606 B2 | 10/2011 | Park et al. |
| 8,104,478 B2 | 1/2012 | Pflueger et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,383,201 B2 | 2/2013 | Berry et al. |
| 8,420,074 B2 | 4/2013 | Rehberger et al. |
| 8,454,729 B2 | 6/2013 | Mittelmark et al. |
| 8,481,299 B2 | 7/2013 | Gueniche et al. |
| 8,496,914 B2 | 7/2013 | Bonfiglio |
| 8,584,685 B2 | 11/2013 | Kovarik et al. |
| 8,585,588 B2 | 11/2013 | Kovarik et al. |
| 8,591,412 B2 | 11/2013 | Kovarik et al. |
| 8,657,879 B2 | 2/2014 | Shalon et al. |
| 8,685,389 B2 | 4/2014 | Baur et al. |
| 8,701,671 B2 | 4/2014 | Kovarik |
| 8,716,327 B2 | 5/2014 | Zhao et al. |
| 8,757,173 B2 | 6/2014 | Kovarik et al. |
| 8,758,764 B2 | 6/2014 | Masignani et al. |
| 8,815,538 B2 | 8/2014 | Lanzalaco et al. |
| 8,829,165 B2 | 9/2014 | Jackson et al. |
| 8,859,741 B2 | 10/2014 | Jackson et al. |
| 8,865,211 B2 | 10/2014 | Tzannis et al. |
| 8,936,030 B2 | 1/2015 | Kovarik et al. |
| 8,945,839 B2 | 2/2015 | Zhang et al. |
| 8,951,775 B2 | 2/2015 | Castiel et al. |
| 8,999,372 B2 | 4/2015 | Davidson et al. |
| 9,010,340 B2 | 4/2015 | Kovarik et al. |
| 9,011,834 B1 | 4/2015 | McKenzie et al. |
| 9,016,221 B2 | 4/2015 | Brennan et al. |
| 9,017,718 B2 | 4/2015 | Tan et al. |
| 9,028,841 B2 | 5/2015 | Henn et al. |
| 9,044,420 B2 | 6/2015 | Dubensky, Jr. |
| 9,045,547 B2 | 6/2015 | Jackson et al. |
| 9,056,912 B2 | 6/2015 | Grandi et al. |
| 9,095,704 B2 | 8/2015 | McGuire et al. |
| 9,131,884 B2 | 9/2015 | Holmes et al. |
| 9,149,429 B2 | 10/2015 | Kovacs et al. |
| 9,234,204 B2 | 1/2016 | Qvit-Raz et al. |
| 9,254,295 B2 | 2/2016 | Adams et al. |
| 9,288,981 B2 | 3/2016 | Gandhi et al. |
| 9,295,682 B2 | 3/2016 | Nunes et al. |
| 9,314,489 B2 | 4/2016 | Kelly et al. |
| 9,408,880 B2 | 8/2016 | Kovarik et al. |
| 9,445,936 B2 | 9/2016 | Kovarik |
| 9,457,077 B2 | 10/2016 | Kovarik et al. |
| 9,549,842 B2 | 1/2017 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik et al. |
| 9,795,641 B2 | 10/2017 | Nardelli et al. |
| 9,987,224 B2 | 6/2018 | Kovarik et al. |
| 10,085,938 B2 | 10/2018 | Kovarik et al. |
| 10,086,018 B2 | 10/2018 | Kovarik |
| 10,111,913 B2 | 10/2018 | Kovarik |
| 10,195,273 B2 | 2/2019 | Clube |
| 10,245,288 B2 | 4/2019 | Kovarik |
| 10,314,865 B2 | 6/2019 | Kovarik |

(56) References Cited

U.S. PATENT DOCUMENTS

| | | |
|---|---|---|
| 10,314,866 B2 | 6/2019 | Kovarik |
| 10,512,661 B2 | 12/2019 | Kovarik |
| 10,548,761 B2 | 2/2020 | Kovarik |
| 10,555,976 B2 | 2/2020 | Kovarik |
| 10,668,014 B2 | 6/2020 | Kovarik et al. |
| 10,683,323 B2 | 6/2020 | Prakash et al. |
| 10,687,975 B2 | 6/2020 | Kovarik et al. |
| 10,716,815 B2 | 7/2020 | Kovarik et al. |
| 10,730,827 B2 | 8/2020 | Wortmann et al. |
| 10,760,075 B2 | 9/2020 | Sommer et al. |
| 10,835,560 B2 | 11/2020 | Kovarik |
| 10,842,834 B2 | 11/2020 | Kovarik |
| 10,864,109 B2 | 12/2020 | Kovarik |
| 10,940,169 B2 | 3/2021 | Kovarik et al. |
| 11,026,982 B2 | 6/2021 | Kovarik |
| 11,083,760 B2 | 8/2021 | Han |
| 11,213,552 B2 | 1/2022 | Kovarik |
| 11,273,187 B2 | 3/2022 | Kovarik |
| 11,357,722 B2 | 6/2022 | Kovarik et al. |
| 11,419,903 B2 | 8/2022 | Kovarik |
| 11,523,934 B2 | 12/2022 | Kovarik et al. |
| 11,529,379 B2 | 12/2022 | Kovarik |
| 11,642,382 B2 | 5/2023 | Kovarik |
| 11,672,835 B2 | 6/2023 | Kovarik |
| 2002/0009520 A1 | 1/2002 | Clayton et al. |
| 2002/0022057 A1 | 2/2002 | Battey et al. |
| 2002/0037310 A1 | 3/2002 | Jonn et al. |
| 2002/0044988 A1 | 4/2002 | Fuchs et al. |
| 2003/0031737 A1 | 2/2003 | Rosenbloom |
| 2003/0062050 A1 | 4/2003 | Schmidt |
| 2003/0083287 A1 | 5/2003 | Burgess et al. |
| 2003/0104041 A1 | 6/2003 | Hsu et al. |
| 2003/0106243 A1 | 6/2003 | Tucker |
| 2003/0124178 A1 | 7/2003 | Haley |
| 2003/0140930 A1 | 7/2003 | Knudson et al. |
| 2003/0149387 A1 | 8/2003 | Barakat et al. |
| 2003/0149445 A1 | 8/2003 | Knudson et al. |
| 2003/0206995 A1 | 11/2003 | Bowling et al. |
| 2004/0053352 A1 | 3/2004 | Ouyang et al. |
| 2004/0057962 A1 | 3/2004 | Timmerman |
| 2004/0096569 A1 | 5/2004 | Barkalow et al. |
| 2004/0110111 A1 | 6/2004 | Wasylucha |
| 2004/0115223 A1 | 6/2004 | Follansbee |
| 2004/0120991 A1 | 6/2004 | Gardner et al. |
| 2004/0136923 A1 | 7/2004 | Davidson et al. |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0180080 A1 | 9/2004 | Furasawa et al. |
| 2004/0224007 A1 | 11/2004 | Zhang |
| 2004/0228804 A1 | 11/2004 | Jones et al. |
| 2005/0004417 A1 | 1/2005 | Nelson et al. |
| 2005/0159637 A9 | 1/2005 | Nelson et al. |
| 2005/0118655 A1 | 6/2005 | Weinstock et al. |
| 2005/0137109 A1 | 6/2005 | Quan et al. |
| 2005/0196358 A1 | 9/2005 | Georgiades et al. |
| 2005/0260544 A1 | 11/2005 | Jones et al. |
| 2006/0018843 A1 | 1/2006 | Fine |
| 2006/0035008 A1 | 2/2006 | Virgallito et al. |
| 2006/0064903 A1 | 3/2006 | Tucker |
| 2006/0127330 A1 | 6/2006 | Tsuchida et al. |
| 2006/0188813 A1 | 8/2006 | Shimada |
| 2006/0204591 A1 | 9/2006 | Burrel et al. |
| 2006/0207721 A1 | 9/2006 | Slominski et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis et al. |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0093420 A1 | 4/2007 | Yeomans et al. |
| 2007/0098744 A1 | 5/2007 | Knorr et al. |
| 2007/0102010 A1 | 5/2007 | Lemperle et al. |
| 2007/0122455 A1 | 5/2007 | Myers et al. |
| 2007/0123448 A1 | 5/2007 | Kaplan et al. |
| 2007/0148136 A1 | 6/2007 | Whitlock |
| 2007/0202057 A1 | 8/2007 | Fankhauser et al. |
| 2007/0207955 A1 | 9/2007 | Tanihara et al. |
| 2007/0218114 A1 | 9/2007 | Duggan |
| 2007/0227545 A1 | 10/2007 | Conrad et al. |
| 2007/0231923 A1 | 10/2007 | Cumberland et al. |
| 2007/0246052 A1 | 10/2007 | Hegde et al. |
| 2007/0261701 A1 | 11/2007 | Sanders |
| 2007/0280964 A1 | 12/2007 | Knorr et al. |
| 2007/0293587 A1 | 12/2007 | Haley |
| 2007/0295340 A1 | 12/2007 | Buscemi |
| 2008/0032253 A1 | 2/2008 | Montgomery et al. |
| 2008/0075825 A1 | 3/2008 | Fuisz et al. |
| 2008/0112983 A1 | 5/2008 | Bufe et al. |
| 2008/0242543 A1 | 10/2008 | Banerjee et al. |
| 2008/0267933 A1 | 10/2008 | Ohlson et al. |
| 2008/0286210 A1 | 11/2008 | He et al. |
| 2008/0305089 A1 | 12/2008 | Bufe et al. |
| 2009/0004275 A1 | 1/2009 | Martyn et al. |
| 2009/0098192 A1 | 4/2009 | Fuisz |
| 2009/0130199 A1 | 5/2009 | Kovacs et al. |
| 2009/0148482 A1 | 6/2009 | Peters |
| 2009/0196907 A1 | 8/2009 | Bunick et al. |
| 2009/0196908 A1 | 8/2009 | Lee et al. |
| 2009/0205083 A1 | 8/2009 | Gupta et al. |
| 2010/0029832 A1 | 2/2010 | Pinnavaia et al. |
| 2010/0040593 A1 | 2/2010 | Hedman et al. |
| 2010/0040712 A1 | 2/2010 | Fisher |
| 2010/0081681 A1 | 4/2010 | Blagosklonny |
| 2010/0092406 A1 | 4/2010 | Perez-Davidi et al. |
| 2010/0143447 A1 | 6/2010 | Hansen et al. |
| 2010/0229876 A1 | 9/2010 | Knudson et al. |
| 2010/0247644 A1 | 9/2010 | Domb et al. |
| 2010/0260720 A1 | 10/2010 | Sprenger |
| 2010/0285098 A1 | 11/2010 | Haley |
| 2011/0009834 A1 | 1/2011 | Asmussen et al. |
| 2011/0033542 A1 | 2/2011 | Myers et al. |
| 2011/0088701 A1 | 4/2011 | Thornton |
| 2011/0100378 A1 | 5/2011 | Rousseau |
| 2011/0142942 A1 | 6/2011 | Schobel et al. |
| 2011/0217368 A1 | 9/2011 | Prakash et al. |
| 2011/0230587 A1 | 9/2011 | MacInnis et al. |
| 2011/0230727 A1 | 9/2011 | Sanders et al. |
| 2011/0250626 A1 | 10/2011 | Williams et al. |
| 2011/0274795 A1 | 11/2011 | Bogue et al. |
| 2011/0290694 A1 | 12/2011 | Fuisz et al. |
| 2012/0027786 A1 | 2/2012 | Gupta et al. |
| 2012/0029832 A1 | 2/2012 | Dodgson |
| 2012/0039806 A1 | 2/2012 | Lahoud et al. |
| 2012/0058094 A1 | 3/2012 | Blaser et al. |
| 2012/0128597 A1 | 5/2012 | Peters et al. |
| 2012/0142548 A1 | 6/2012 | Corsi et al. |
| 2012/0148629 A1 | 6/2012 | Holvoet et al. |
| 2012/0276143 A1 | 11/2012 | O'Mahony et al. |
| 2012/0276149 A1 | 11/2012 | Littman et al. |
| 2012/0276525 A1 | 11/2012 | Kovarik et al. |
| 2012/0283269 A1 | 11/2012 | Blagosklonny et al. |
| 2012/0294822 A1 | 11/2012 | Russo et al. |
| 2012/0301452 A1 | 11/2012 | Gueniche et al. |
| 2013/0059815 A1 | 3/2013 | Fournell et al. |
| 2013/0087155 A1 | 4/2013 | Hedman et al. |
| 2013/0157876 A1 | 6/2013 | Lynch et al. |
| 2013/0225440 A1 | 8/2013 | Friedman et al. |
| 2013/0236488 A1 | 9/2013 | Dashper et al. |
| 2013/0252983 A1 | 9/2013 | Cerione et al. |
| 2013/0259834 A1 | 10/2013 | Klaenhammer et al. |
| 2013/0310416 A1 | 11/2013 | Blagosklonny |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon et al. |
| 2014/0065209 A1 | 3/2014 | Putaala et al. |
| 2014/0065218 A1 | 3/2014 | Lang et al. |
| 2014/0066817 A1 | 3/2014 | Kovarik et al. |

(56) References Cited

U.S. PATENT DOCUMENTS

| | | |
|---|---|---|
| 2014/0068797 A1 | 3/2014 | Doudna et al. |
| 2014/0125550 A1 | 5/2014 | Kaneko et al. |
| 2014/0154290 A1 | 6/2014 | Peters et al. |
| 2014/0199266 A1 | 7/2014 | Park et al. |
| 2014/0255351 A1 | 9/2014 | Berstad et al. |
| 2014/0271867 A1 | 9/2014 | Myers et al. |
| 2014/0294915 A1 | 10/2014 | Barreca et al. |
| 2014/0296139 A1 | 10/2014 | Cohen et al. |
| 2014/0333003 A1 | 11/2014 | Allen et al. |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0017143 A1 | 1/2015 | Holvoet et al. |
| 2015/0017227 A1 | 1/2015 | Kim et al. |
| 2015/0038594 A1 | 2/2015 | Borges et al. |
| 2015/0045546 A1 | 2/2015 | Siksnys et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0093473 A1 | 4/2015 | Barrangou et al. |
| 2015/0132263 A1 | 5/2015 | Liu et al. |
| 2015/0147371 A1 | 5/2015 | Kovarik et al. |
| 2015/0150792 A1 | 6/2015 | Klingman |
| 2015/0166641 A1 | 6/2015 | Goodman et al. |
| 2015/0190435 A1 | 7/2015 | Henn et al. |
| 2015/0202136 A1 | 7/2015 | Lanzalaco et al. |
| 2015/0216917 A1 | 8/2015 | Jones et al. |
| 2015/0224072 A1 | 8/2015 | Pellikaan |
| 2015/0252358 A1 | 9/2015 | Maeder et al. |
| 2015/0259728 A1 | 9/2015 | Cutliffe et al. |
| 2015/0329555 A1 | 11/2015 | Liras et al. |
| 2015/0329875 A1 | 11/2015 | Gregory et al. |
| 2015/0352023 A1 | 12/2015 | Berg et al. |
| 2015/0353901 A1 | 12/2015 | Liu et al. |
| 2015/0361436 A1 | 12/2015 | Hitchcock et al. |
| 2015/0374607 A1 | 12/2015 | Lanzalaco et al. |
| 2016/0000754 A1 | 1/2016 | Stamets |
| 2016/0000841 A1 | 1/2016 | Yamamoto et al. |
| 2016/0008412 A1 | 1/2016 | Putaala et al. |
| 2016/0024510 A1 | 1/2016 | Bikard et al. |
| 2016/0040216 A1 | 2/2016 | Akins et al. |
| 2016/0069921 A1 | 3/2016 | Holmes et al. |
| 2016/0089315 A1 | 3/2016 | Kleinberg et al. |
| 2016/0089405 A1 | 3/2016 | Lue |
| 2016/0095316 A1 | 4/2016 | Goodman et al. |
| 2016/0120915 A1 | 5/2016 | Blaser et al. |
| 2016/0122806 A1 | 5/2016 | Amini et al. |
| 2016/0151427 A1 | 6/2016 | Whitlock et al. |
| 2016/0151428 A1 | 6/2016 | Bryan |
| 2016/0158294 A1 | 6/2016 | Von Maltzahn et al. |
| 2016/0168594 A1 | 6/2016 | Zhang et al. |
| 2016/0175327 A1 | 6/2016 | Adams et al. |
| 2016/0199424 A1 | 7/2016 | Berry et al. |
| 2016/0206564 A1 | 7/2016 | Trachtman |
| 2016/0206666 A1 | 7/2016 | Falb et al. |
| 2016/0206668 A1 | 7/2016 | Kort et al. |
| 2016/0213702 A1 | 7/2016 | Von Maltzahn et al. |
| 2016/0243132 A1 | 8/2016 | Adams et al. |
| 2016/0271106 A1 | 9/2016 | Shi et al. |
| 2016/0271189 A1 | 9/2016 | Cutcliffe et al. |
| 2016/0311913 A1 | 10/2016 | Sun et al. |
| 2016/0314281 A1 | 10/2016 | Apte et al. |
| 2016/0354416 A1 | 12/2016 | Gajewski et al. |
| 2016/0374941 A1 | 12/2016 | Barreca et al. |
| 2017/0014341 A1 | 1/2017 | Armer et al. |
| 2017/0020932 A1 | 1/2017 | Cutcliffe et al. |
| 2017/0027914 A1 | 2/2017 | Qi |
| 2017/0042860 A1 | 2/2017 | Kashyap et al. |
| 2017/0042924 A1 | 2/2017 | Otsuka et al. |
| 2017/0071986 A1 | 3/2017 | Kovarik et al. |
| 2017/0079947 A1 | 3/2017 | Richards |
| 2017/0100328 A1 | 4/2017 | Kovarik et al. |
| 2017/0232043 A1 | 8/2017 | Falb et al. |
| 2017/0240625 A1 | 8/2017 | Zeller et al. |
| 2017/0246269 A1 | 8/2017 | Hajishengallis et al. |
| 2017/0298115 A1 | 10/2017 | Loomis et al. |
| 2017/0312232 A1 | 11/2017 | Vitetta et al. |
| 2017/0342141 A1 | 11/2017 | Russo et al. |
| 2017/0348303 A1 | 12/2017 | Bosse et al. |
| 2018/0000878 A1 | 1/2018 | Goodman et al. |
| 2018/0015131 A1 | 1/2018 | Gajewski et al. |
| 2018/0016647 A1 | 1/2018 | Van Sinderen et al. |
| 2018/0092899 A1 | 4/2018 | Liu et al. |
| 2018/0100169 A1 | 4/2018 | Soucaille et al. |
| 2018/0110795 A1 | 4/2018 | Frias-Lopez |
| 2018/0111984 A1 | 5/2018 | Bigal et al. |
| 2018/0127490 A1 | 5/2018 | Bigal et al. |
| 2018/0134772 A1 | 5/2018 | Sharma et al. |
| 2018/0140698 A1 | 5/2018 | Clube et al. |
| 2018/0207165 A1 | 7/2018 | Harmsen et al. |
| 2018/0235987 A1 | 8/2018 | Von Maltzahn et al. |
| 2018/0258100 A1 | 9/2018 | Gregory et al. |
| 2018/0296582 A1 | 10/2018 | von Maltzahn et al. |
| 2018/0303658 A1 | 10/2018 | Kovarik et al. |
| 2018/0312851 A1 | 11/2018 | Falb et al. |
| 2018/0326008 A1 | 11/2018 | Schreiber et al. |
| 2018/0371405 A1 | 12/2018 | Barrangou et al. |
| 2019/0000815 A1 | 1/2019 | Melin |
| 2019/0018012 A1 | 1/2019 | Kovarik |
| 2019/0059314 A1 | 2/2019 | Aharoni et al. |
| 2019/0290605 A1 | 6/2019 | Rasochova et al. |
| 2019/0120960 A1 | 7/2019 | Konradi et al. |
| 2019/0262298 A1 | 8/2019 | Kanthasamy et al. |
| 2019/0315642 A1 | 10/2019 | Parsley et al. |
| 2019/0388471 A1 | 12/2019 | June et al. |
| 2019/0390284 A1 | 12/2019 | Kim |
| 2020/0009185 A1 | 1/2020 | Shin et al. |
| 2020/0009268 A1 | 1/2020 | Scholz |
| 2020/0032224 A1 | 1/2020 | Schaefer et al. |
| 2020/0148642 A1 | 5/2020 | Konradi et al. |
| 2020/0155447 A1 | 5/2020 | Edwards |
| 2020/0188454 A1 | 6/2020 | Slykerman |
| 2020/0190494 A1 | 6/2020 | Hou et al. |
| 2020/0197215 A1 | 6/2020 | Kovarik et al. |
| 2020/0199555 A1 | 6/2020 | Zhang |
| 2021/0169954 A1 | 6/2021 | Balani et al. |
| 2021/0198665 A1 | 7/2021 | Sommer et al. |
| 2021/0308028 A1 | 10/2021 | Yang et al. |
| 2021/0321756 A1 | 10/2021 | McLaughlin et al. |
| 2021/0361560 A1 | 11/2021 | Krueger et al. |
| 2021/0386659 A1 | 12/2021 | Kim |
| 2022/0000760 A1 | 1/2022 | Rasochova |
| 2022/0023259 A1 | 1/2022 | Davidson et al. |
| 2022/0031590 A1 | 2/2022 | Pesaro et al. |
| 2022/0031767 A1 | 2/2022 | Duportet et al. |
| 2022/0071877 A1 | 3/2022 | Zenobia et al. |
| 2022/0088001 A1 | 3/2022 | Kovarik et al. |
| 2022/0088090 A1 | 3/2022 | Lobacki et al. |
| 2022/0118031 A1 | 4/2022 | Kovarik |
| 2022/0135987 A1 | 5/2022 | Leveau et al. |
| 2022/0193150 A1 | 6/2022 | Kovarik |
| 2022/0193157 A1 | 6/2022 | Zimmerman et al. |
| 2022/0257410 A1 | 8/2022 | Kovarik |
| 2022/0296500 A1 | 9/2022 | Kovarik |
| 2022/0331374 A1 | 10/2022 | Richter et al. |
| 2022/0339208 A1 | 10/2022 | Abel et al. |
| 2022/0387402 A1 | 12/2022 | Aspnes et al. |
| 2023/0040879 A1 | 2/2023 | Kovarik |
| 2023/0106721 A1 | 4/2023 | Catania et al. |
| 2023/0131201 A1 | 4/2023 | Kovarik |
| 2023/0165706 A1 | 6/2023 | Tye et al. |
| 2023/0218682 A1 | 7/2023 | Tye et al. |
| 2023/0241129 A1 | 8/2023 | Simmons et al. |

FOREIGN PATENT DOCUMENTS

| | | |
|---|---|---|
| JP | S56-100714 | 8/1981 |
| WO | WO 98/22097 | 5/1998 |
| WO | WO 2006/007922 | 1/2006 |
| WO | WO 2006/015445 | 2/2006 |
| WO | WO 2006/133879 | 12/2006 |

(56) References Cited

FOREIGN PATENT DOCUMENTS

| WO | WO 2008/088426 | 7/2008 |
|---|---|---|
| WO | WO 2008/097890 | 8/2008 |
| WO | WO 2009/052421 | 4/2009 |
| WO | WO 2010/041143 | 4/2010 |
| WO | WO 2011/020780 | 2/2011 |
| WO | WO 2011/029701 | 3/2011 |
| WO | WO 2013/026000 | 2/2013 |
| WO | WO 2013/107750 | 7/2013 |
| WO | WO 2013/182038 | 12/2013 |
| WO | WO 2014/103488 | 7/2014 |
| WO | WO 2014/152338 | 9/2014 |
| WO | WO 2014/182632 | 11/2014 |
| WO | WO 2014/196913 | 12/2014 |
| WO | WO 2015/069682 | 5/2015 |
| WO | WO 2016/070151 | 5/2016 |
| WO | WO 2017/211753 | 12/2017 |
| WO | WO 2019/067621 | 4/2019 |
| WO | WO 2022/187274 | 9/2022 |

OTHER PUBLICATIONS

U.S. Appl. No. 18/143,399, filed May 4, 2023, Kovarik.
U.S. Appl. No. 18/232,433, filed Aug. 10, 2023, Simmons et al.
"Oral Cavity," University of Michigan Medical School, Date Unknown, retrieved Nov. 20, 2019 from https://histology.medicine.umich.edu/resources/oral-cavity, 5 pages.
"The structure behind the simplicity of CRISPR/Cas9," The Scinder at Medium.com, Dec. 23, 2015, retrieved from https://medium.com/the-scinder/the-structure-behind-the-simplicity-of-crispr-cas9-6f8cb60695c4, 8 pages.
Abruzzo et al., "Influence of Lactobacillus Biosurfactants on Skin Permeation of Hydrocortisone," Pharmaceutics, vol. 13, No. 6, May 2021, 14 pages.
Agrawal et al., "Technique to Control pH in Vicinity of Biodegrading PLA-PGA Implants," Journal of Biomedical Materials Research, vol. 38, No. 2, 1997, pp. 105-114.
Aguilar-Toala et al., "Potential role of natural bioactive peptides for development of cosmeceutical skin products," Peptides, vol. 122, No. 170170, Dec. 2019, 8 pages. Abstract only.
Athanasiou et al., "In Vitro Degradation and Release Characteristics of Biodegradable Implants Containing Trypsin Inhibitor," Clinical Orthopaedics and Related Research, vol. 315, Jun. 1995, pp. 272-281. Abstract only.
Auerbach et al., "Angiogenesis assays: Problems and pitfalls," Cancer and Metastasis Reviews, vol. 19, 2000, pp. 167-172.
Basseri et al., "Antibiotics for the Treatment of Irritable Bowel Syndrome," Gastroenterology & Hepatology, vol. 7, No. 7, Jul. 2011, pp. 455-493.
Baud et al., "Microbial diversity in the vaginal microbiota and its link to pregnancy outcomes," Scientific Reports, vol. 13, No. 9061, 2023, 12 pages.
Blumen et al., "Radiofrequency Ablation for the Treatment of Mild to Moderate Obstructive Sleep Apnea," The Laryngoscope, vol. 112, No. 11, Nov. 2002, pp. 2086-2092.
Bocheva et al., "Protective Role of Melatonin and Its Metabolites in Skin Aging," International Journal of Molecular Sciences, vol. 23, No. 1238, Jan. 2022, 23 pages.
Brietzke et al., "Injection Snoreplasty: Extended Follow-Up and New Objective Data," Otolaryngology—Head and Neck Surgery, vol. 128, No. 5, May 2003, pp. 605-615. Abstract only.
Brietzke et al., "Injection Snoreplasty: How to Treat Snoring without All the Pain and Expense," Otolaryngology—Head and Neck Surgery, vol. 124, No. 5, May 2001, pp. 503-510. Abstract only.
Brietzke et al., "Injection Snoreplasty: Investigation of Alternative Sclerotherapy Agents," Otolaryngology—Head and Neck Surgery, vol. 130, No. 1, Jan. 2004, pp. 47-57. Abstract only.
Brown et al., "Improving the Diagnosis of Vulvovaginitis: Perspectives to Align Practice, Guidelines, and Awareness," Population Health Management, vol. 23, Suppl. 1, 2020, pp. S3-S12.
Catalano et al., "Additional palatal implants for refractory snoring," Otolaryngology—Head and Neck Surgery, vol. 137, No. 1, Jul. 2007, pp. 105-109. Abstract only.
Charulatha et al., "Influence of different crosslinking treatments on the physical properties of collagen membranes," Biomaterials, vol. 24, No. 5, 2003, pp. 759-767.
Chen et al., "Targeting Aldehyde Dehydrogenase 2: New Therapeutic Opportunities," Physiological Reviews, vol. 94, No. 1, 2014, 65 pages.
Choi et al., "Therapeutic Effects of Cold-Pressed Perilla Oil Mainly Consisting of Linolenic acid, Oleic Acid and Linoleic Acid on UV-Induced Photoaging in NHDF Cells and SKH-1 Hairless Mice," Molecules, vol. 25, Feb. 2020, 19 pages.
Chuang et al., "Effects of exogenous crosslinking on in vitro tensile and compressive moduli of lumbar intervertebral discs," Clinical Biomechanics, vol. 22, No. 1, Jan. 2007, pp. 14-20. Abstract only.
Courage, "Fiber-Famished Gut Microbes Linked to Poor Health," Scientific American, Mar. 23, 2015, retrieved from https://www.scientificamerican.com/article/fiber-famished-gut-microbes-linked-to-poor-health, 10 pages.
De Seta et al., "The Vaginal Community State Types Microbiome-Immune Network as Key Factor for Bacterial Vaginosis and Aerobic Vaginitis," Frontiers in Microbiology, vol. 10, No. 2451, Oct. 30, 2019, 8 pages.
Ding et al., "Resveratrol accelerates wound healing by inducing M2 macrophage polarisation in diabetic mice," Pharmaceutical Biology, vol. 60, No. 1, 2022, pp. 2328-2337.
Douam et al., "Genetic Dissection of the Host Tropism of Human-Tropic Pathogens," Annual Review of Genetics, vol. 49, 2015, pp. 21-45.
Dunkley et al., "A role for CD4+ T cells from orally immunized rats in enhanced clearance of Pseudomonas aeruginosa from the lung," Immunology, vol. 83, 1994, pp. 362-369.
Earlia et al., "GC/MS Analysis of Fatty Acids on Pliek U Oil and Its Pharmacological Study by Molecular Docking to Filaggrin as a Drug Candidate in Atopic Dermatitis Treatment," Scientific World Journal, Nov. 2019, 7 pages.
Enomoto et al., "Koji amazake Maintains Water Content in the Left Cheek Skin of Healthy Adults: A Randomized, Double-Blind, Placebo-Controlled, Parallel-Group, Comparative Trial," Clinical, Cosmetic and Investigational Dermatology, vol. 15, Jul. 2022, pp. 1283-1291.
Farhadihosseinabadi et al., "The in vivo effect of Lacto-N-neotetraose (LNnT) on the expression of type 2 immune response involved genes in the wound healing process," Scientific Reports, vol. 10, No. 997, Jan. 2020, 11 pages.
Fischer et al., "[Radiofrequency ablation of the soft palate (somnoplasty). A new method in the treatment of habitual and obstructive snoring].," HNO, vol. 48, No. 1, Jan. 2000, pp. 33-40. Abstract only.
Friedman et al., "Patient Selection and Efficacy of Pillar Implant Technique for Treatment of Snoring and Obstructive Sleep Apnea/Hypopnea Syndrome," Otolaryngology—Head and Neck Surgery, vol. 134, No. 2, Feb. 2006, pp. 187-196. Abstract only.
Gajer et al., "Temporal Dynamics of the Human Vaginal Microbiota," Science Translational Medicine, vol. 4, No. 132, May 2, 2012, 21 pages.
Gratzer et al., "Control of pH Alters the Type of Cross-linking Produced by 1-Ethyl-3-(3-Dimethylaminopropyl)-Carbodiimide (EDC) Treatment of Acellular Matrix Vascular Grafts," Journal of Biomedical Materials Research, vol. 58, No. 2, 2001, pp. 172-179.
Guilleminault et al., "Snoring (I). Daytime sleepiness in regular heavy snorers," Chest, vol. 99, 1991, pp. 40-48.
Guilleminault et al., "The sleep apnea syndromes," Annual Review of Medicine, vol. 27, Feb. 1976, pp. 465-484. First Page Only.
Gura, "Systems for Identifying New Drugs Are Often Faulty," Science, vol. 278, No. 5340, Nov. 7, 1997, pp. 1041-1042.
Han et al., "Proanthocyanidin: A natural crosslinking reagent for stabilizing collagen matrices," Journal of Biomedical Materials Research, vol. 65A, No. 1, Apr. 2003, pp. 118-124. Abstract only.
Hedman et al., "Exogenous Cross-Linking Increases the Stability of Spinal Motion Segments," Spine, vol. 31, No. 15, Jul. 2006, pp. E480-E485. Abstract only.

(56) References Cited

OTHER PUBLICATIONS

Hennessy et al., "Statins as next generation anti-microbials: Is there potential for repurposing?," Antimicrob. Agents Chemother., Jun. 20, 2016, 46 pages.
Hildebrand et al., "Vaginitis," NCBI Bookshelf, Updated Nov. 14, 2022, 12 pages.
Hoffmann et al., "Glutaraldehyde and oxidised dextran as crosslinker reagents for chitosan-based scaffolds for cartilage tissue engineering," Journal of Materials Science: Materials in Medicine, vol. 20, Mar. 2009, pp. 1495-1503.
Hunter et al., "Meniscal material properties are minimally affected by matrix stabilization using glutaraldehyde and glycation with ribose," Journal of Orthopaedic Research, vol. 23, 2005, pp. 555-561.
Jain, "Barriers to Drug Delivery in Solid Tumors," Scientific American, Jul. 1994, pp. 58-65.
Kilkkinen et al., "Use of antimicrobials and risk of type 1 diabetes in a population-based mother-child cohort," Diabetologia, vol. 49, 2006, pp. 66-70.
Kim et al., "Kaempferol tetrasaccharides restore skin atrophy via PDK1 inhibition in human skin cells and tissues: Bench and clinical studies," Biomedicine & Pharmacotherapy, vol. 156, No. 113864, Dec. 2022, 13 pages.
Kim et al., "Spermidine-induced recovery of human dermal structure and barrier function by skin microbiome," Communications Biology, vol. 4, No. 231, 2021, 11 pages.
Kim et al., "β-Glucogallin isolated from Fusidium coccineum and its enhancement of skin barrier effects," Applied Biological Chemistry, vol. 63, No. 77, Nov. 2020, 7 pages.
Kimoto et al., "New Lactococcus Strain with Immunnomodulatory Activity: Enhancement of Th1-Type Immune Response," Microbiol. Immunol., vol. 48, No. 2, 2004, pp. 75-82.
Klapperich et al., "A novel biocompatible adhesive incorporating plant-derived monomers," Journal of Biomedical Materials Research Part A, vol. 91, No. 2, pp. 378-374.
Klingspor et al., "Research Article: Enterococcus faecium NCIMB 10415 Modulates Epithelial Integrity, Heat Shock Protein, and Proinflammatory Cytokine Response in Intestinal Cells," Mediators of Inflammation, vol. 2015, No. 304149, 2015, 12 pages.
Ko, "Effects of Glycogen on Ceramide Production in Cultured Human Keratinocytes via Acid Sphingomyelinase Activation," Master's Thesis Submitted to the Graduate School of Public Health (Korea), 2018, 53 pages.
Komuro et al., "Sphingomyelin maintains the cutaneous barrier via regulation of the STAT3 pathway," The FASEB Journal, vol. 36, No. 4, Apr. 2022, 17 pages.
Kurek-Gorecka et al., "Bee Products in Dermatology and Skin Care," Molecules, vol. 25, No. 3, Jan. 2020, 17 pages.
Kyriakopoulos et al., "Taurine and N-Bromotaurine in Topical Treatment of Psoriasis," Advances in Experimental Medicine and Biology, vol. 1370, 2022, pp. 99-111. Abstract only.
Laneri et al., "Plant cell culture extract of Cirsium eriophorum with skin pore refiner activity by modulating sebum production and inflammatory response," Phytotherapy Research, vol. 35, No. 1, Jan. 2021, pp. 530-540.
Lebeer et al., "Selective targeting of skin pathobionts and inflammation with topically applied lactobacilli," Cell Reports Medicine, vol. 3, No. 2, Feb. 2022, 22 pages.
Lenger et al., "D-mannose vs other agents for recurrent urinary tract infection prevention in adult women: a systematic review and meta-analysis," American Journal of Obstetrics and Gynecology, vol. 223, No. 2, Aug. 2020, pp. 265.e1-265.e13.
Lew et al., "Bioactives from probiotics for dermal health: functions and benefits," Journal of Applied Microbiology, vol. 114, No. 5, May 2013, pp. 1241-1253.
Lewis et al., "Vaginal Microbiome and Its Relationship to Behavior, Sexual Health, and Sexually Transmitted Diseases," Obstetrics & Gynecology, vol. 129, No. 4, Apr. 2017, pp. 643-654.
Liu et al., "Activation of aryl hydrocarbon receptor in Langerhans cells by a microbial metabolite of tryptophan negatively regulates skin inflammation," Journal of Dermatological Science, vol. 100, No. 3, Dec. 2020, pp. 192-200. Abstract only.
Liu et al., "The potential of Streptococcus thermophiles (TCI633) in the anti-aging," Journal of Cosmetic Dermatology, vol. 21, No. 6, Jun. 2022, pp. 2635-2647.
Ma et al., "The vaginal microbiome: rethinking health and diseases," Annual Review of Microbiology, vol. 66, 2012, pp. 371-389.
Mach et al., "Endurance exercise and gut microbiota: A review," Journal of Sport and Health Science, vol. 6, No. 2, Jun. 2017, pp. 179-197.
Mahdiani et al., "Protective effect of luteolin against chemical and natural toxicants by targeting NF-κB pathway," Biofactors, vol. 48, No. 4, Jul. 2022, pp. 744-762. Abstract only.
Malaguarnera et al., "Bifidobacterium longum with Fructo-Oligosaccharides in Patients with Non Alcoholic Steatohepatitis," Digestive Diseases and Sciences, vol. 57, 2012, pp. 545-553.
Matsui et al., "Biological Rhythms in the Skin," International Journal of Molecular Sciences, vol. 17, No. 801, May 2016, 15 pages.
Mayrovitz et al., "Assessing Potential Circadian, Diurnal, and Ultradian Variations in Skin Biophysical Properties," Cureus, vol. 13, No. 9, Sep. 2021, 18 pages.
McFadzean, "Exercise can help modulate human gut microbiota," Honors Thesis Submitted to the University of Colorado Department of Evolutionary Biology, Apr. 7, 2014, 34 pages.
Nakai et al., "Effects of Topical N-Acetylcysteine on Skin Hydration/Transepidermal Water Loss in Healthy Volunteers and Atopic Dermatitis Patients," Annals of Dermatology, vol. 27, No. 4, Aug. 2015, pp. 450-451.
Neves et al., "Efficacy of a topical serum containing L-ascorbic acid, neohesperidin, pycnogenol, tocopherol, and hyaluronic acid in relation to skin aging signs," Journal of Cosmetic Dermatology, vol. 21, No. 10, Oct. 2022, pp. 4462-4469. Abstract only.
Nisbet et al., "Clinical and in vitro evaluation of new anti-redness cosmetic products in subjects with winter xerosis and sensitive skin," International Journal of Cosmetic Science, vol. 41, No. 6, Dec. 2019, pp. 534-547.
Norton et al., "The immune response to Lactococcus lactis: Implications for its use as a vaccine delivery vehicle," FEMS Microbiology Letters, vol. 120, No. 3, Jul. 15, 1994, pp. 249-256. Abstract only.
O'Hanlon et al., "In vaginal fluid, bacteria associated with bacterial vaginosis can be suppressed with lactic acid but not hydrogen peroxide," BMC Infectious Diseases, vol. 11, No. 200, 2011, 8 pages.
Paladine et al., "Vaginitis: Diagnosis and Treatment," American Family Physician, vol. 97, No. 5, Mar. 1, 2018, pp. 321-329.
Park et al., "Fermented black rice and blueberry with Lactobacillus plantarum MG4221 improve UVB-induced skin injury," Food and Agricultural Immunology, vol. 32, No. 1, 2021, pp. 499-515.
Pinto et al., "Plantaricin A synthesized by Lactobacillus plantarum induces in vitro proliferation and migration of human keratinocytes and increases the expression of TGF-β1, FGF7, VEGF-A and IL-8 genes," Peptides, vol. 32, No. 9, Sep. 2011, pp. 1815-1824. Abstract only.
Ragusa et al., "Spirulina for Skin Care: A Bright Blue Future," Cosmetics, vol. 8, No. 1, Jan. 2021, 19 pages.
Ravel et al., "Vaginal microbiome of reproductive-age women," PNAS, vol. 108, Suppl. 1, Mar. 15, 2011, pp. 4680-4687.
Repa et al., "Mucosal co-application of lactic acid bacteria and allergen induces counter-regulatory immune responses in a murine model of birch pollen allergy," Vaccine, vol. 22, No. 1, 2003, pp. 87-95. Abstract only.
Scaglione et al., "Considerations on D-mannose Mechanism of Action and Consequent Classification of Marketed Healthcare Products," Frontiers In Pharmacology, vol. 12, No. 636377, Mar. 2, 2021, 7 pages.
Schaeffer et al., "Effect of Carbohydrates on Adherence of *Escherichia coli* to Human Urinary Tract Epithelial Cells," Infection and Immunity, vol. 30, No. 2, Nov. 1980, pp. 531-537.
Sevilla et al., "Revisiting the role of melatonin in human melanocyte physiology: A skin context perspective," Journal of Pineal Research, vol. 72, No. 3, Apr. 2022, 23 pages.

(56) References Cited

OTHER PUBLICATIONS

Sheikh, "Is Crispr the Next Antibiotic?," The New York Times, Oct. 29, 2019, retrieved from https://www.nytimes.com/2019/28/health/crispr-genetics-antibiotic-resistance.html, 2 pages.

Shen et al., "Propionibacterium acnes related anti-inflammation and skin hydration activities of madecassoside, a pentacyclic triterpene saponin from Centella asiatica," Bioscience, Biotechnology, and Biochemistry, vol. 83, No. 3, 2019, pp. 561-568.

Sheweita et al., "Preclinical studies on melanogenesis proteins using a resveratrol-nanoformula as a skin whitener," International Journal of Biological Macromolecules, vol. 223, Part A, Dec. 2022, pp. 870-881. Abstract only.

Simmering et al., "The Increase in Hospitalizations for Urinary Tract Infections and the Associated Costs in the United States, 1998-2011," Open Forum Infectious Diseases, vol. 4, No. 1, Feb. 24, 2017, 7 pages.

Sivieri et al., "Lactobacillus acidophilus CRL 1014 improved "gut health" in the SHIME reactor," BMC Gastroenterology, vol. 13, No. 100, 2013, 9 pages.

Spinler et al., "Human-derived probiotic Lactobacillus reuteri demonstrate antimicrobial activities targeting diverse enteric bacterial pathogens," Anaerobe, vol. 14, Feb. 29, 2008, pp. 166-171.

Sporn et al., "Chemoprevention of cancer," Carcinogenesis, vol. 21, No. 3, 2000, pp. 525-530.

Thongaram et al., "Human milk oligosaccharide consumption by probiotic and human-associated bifidobacteria and lactobacilli," Journal of Dairy Science, vol. 100, No. 10, Oct. 2017, pp. 7825-7833.

Traisaeng et al., "A Derivative of Butyric Acid, the Fermentation Metabolite of *Staphylococcus epidermidis*, Inhibits the Growth of a *Staphylococcus aureus* Strain Isolated from Atopic Dermatitis Patients," Toxins, vol. 11, No. 6, May 2019, 12 pages.

Van Der Veer et al., "Comparative genomics of human Lactobacillus crispatus isolates reveals genes for glycosylation and glycogen degradation: implications for in vivo dominance of the vaginal microbiota," Microbiome, vol. 7, No. 49, 2019, 14 pages.

Van Hemert et al., "Migraine associated with gastrointestinal disorders: review of the literature and clinical implications," Frontiers in Neurology, vol. 5, No. 241, Nov. 2014, 4 pages.

Wan et al., "Luteolin-7-glucoside Promotes Human Epidermal Stem Cell Proliferation by Upregulating β-Catenin, c-Myc, and Cyclin Expression," Stem Cells International, vol. 2019, No. 1575480, Jun. 2019, 10 pages.

Wilbie et al., "Delivery Aspects of CRISPR/Cas for in Vivo Genome Editing," Accounts of Chemical Research, vol. 52, 2019, pp. 1555-1564.

Yamamura et al., "Oral mucosal adhesive Film containing local anesthetics: in vitro and clinical evaluation." Journal of Biomedical Materials Research, Fall 1998, vol. 43, No. 3, pp. 313-317. Abstract only.

Yatsuhashi et al., "Effects of Glycogen on Ceramide Production in Cultured Human Keratinocytes via Acid Sphingomyelinase Activation," Journal of Applied Glycoscience, vol. 68, 2021, pp. 41-46.

Yosipovitch et al., "Time-Dependent Variations of the Skin Barrier Function in Humans: Transepidermal Water Loss, Stratum Corneum Hydration, Skin Surface pH, and Skin Temperature," Journal of INvestigative Dermatology, vol. 110, No. 1, Jan. 1998, pp. 20-23.

Zahedi et al., "Development of plasma functionalized polypropylene wound dressing for betaine hydrochloride controlled drug delivery on diabetic wounds," Scientific Reports, vol. 11, No. 9641, 2021, 18 pages.

Zhao et al., "Microbiome-generated amyloid and potential impact on amyloidogenesis in Alzheimer's disease (AD)," Journal of Nature and Science, vol. 1, No. 7, 2015, pp. 1-5.

Zhou et al., "Nicotinamide Mononucleotide Combined With Lactobacillus fermentum TKSN041 Reduces the Photoaging Damage in Murine Skin by Activating AMPK Signaling Pathway," Frontiers in Pharmacology, vol. 12, No. 643089, Mar. 2021, 17 pages.

Official Action for U.S. Appl. No. 14/574,517 dated Jan. 6, 2016, 13 pages.

Notice of Allowance for U.S. Appl. No. 14/574,517, dated Apr. 15, 2016, 8 pages.

Corrected Notice of Allowance for U.S. Appl. No. 14/574,517, dated Jul. 7, 2016, 2 pages.

Official Action for U.S. Appl. No. 14/954,074, dated Jun. 30, 2016, 4 pages.

Notice of Allowance for U.S. Appl. No. 14/954,074, dated Jul. 20, 2016, 7 pages.

Official Action for U.S. Appl. No. 15/270,034, dated Apr. 6, 2017, 5 pages.

Notice of Allowance for U.S. Appl. No. 15/270,034, dated May 5, 2017, 7 pages.

Official Action for U.S. Appl. No. 15/392,173, dated Jan. 22, 2018, 8 pages.

Official Action for U.S. Appl. No. 15/392,173, dated Jul. 6, 2018, 13 pages.

Notice of Allowance for U.S. Appl. No. 15/392,173, dated Dec. 5, 2018, 8 pages.

Official Action for U.S. Appl. No. 16/229,252, dated Feb. 28, 2019, 5 pages.

Notice of Allowance for U.S. Appl. No. 16/229,252, dated Aug. 21, 2019, 7 pages.

Official Action for U.S. Appl. No. 16/722,117, dated Feb. 20, 2020, 6 pages.

Notice of Allowance for U.S. Appl. No. 16/722,117, dated Jul. 30, 2020, 8 pages.

Official Action for U.S. Appl. No. 17/011,175, dated Jun. 17, 2021, 9 pages.

Notice of Allowance for U.S. Appl. No. 17/011,175, dated Nov. 5, 2021, 8 pages.

Official Action for U.S. Appl. No. 17/023,736, dated Nov. 10, 2021, 7 pages.

Notice of Allowance for U.S. Appl. No. 17/023,736, dated Apr. 14, 2022, 8 pages.

Official Action for U.S. Appl. No. 17/893,384, dated May 9, 2023, 8 pages.

Notice of Allowance for U.S. Appl. No. 17/893,384, dated Aug. 23, 2023, 7 pages.

Official Action for U.S. Appl. No. 15/403,823, dated Oct. 30, 2017, 7 pages.

Official Action for U.S. Appl. No. 15/403,823, dated May 25, 2018, 9 pages.

Notice of Allowance for U.S. Appl. No. 15/403,823, dated Jun. 28, 2018, 9 pages.

Official Action for U.S. Appl. No. 16/160,336, dated Nov. 27, 2018, 6 pages.

Notice of Allowance for U.S. Appl. No. 16/160,336, dated Feb. 15, 2019, 7 pages.

Official Action for U.S. Appl. No. 16/423,375, dated Jul. 3, 2019, 6 pages.

Notice of Allowance for U.S. Appl. No. 16/423,375, dated Oct. 16, 2019, 8 pages.

Official Action for U.S. Appl. No. 16/782,364, dated Apr. 9, 2020, 5 pages.

Notice of Allowance for U.S. Appl. No. 16/782,364, dated Jul. 27, 2020, 7 pages.

Official Action for U.S. Appl. No. 16/917,096, dated Jul. 31, 2020, 5 pages.

Official Action for U.S. Appl. No. 16/617,096, dated Oct. 19, 2020, 8 pages.

Official Action for U.S. Appl. No. 17/027,953, dated Jan. 29, 2021, 5 pages.

Notice of Allowance for U.S. Appl. No. 17/027,953, dated Apr. 19, 2021, 8 pages.

Official Action for U.S. Appl. No. 17/337,600, dated Jul. 6, 2021, 5 pages.

Notice of Allowance for U.S. Appl. No. 17/337,600, dated Sep. 9, 2021, 7 pages.

Official Action for U.S. Appl. No. 17/835,204, dated Jul. 28, 2022, 6 pages.

Notice of Allowance for U.S. Appl. No. 17/835,204, dated Aug. 24, 2022, 7 pages.

(56) References Cited

OTHER PUBLICATIONS

Official Action for U.S. Appl. No. 17/848,759, dated Sep. 14, 2022, 6 pages.
Notice of Allowance for U.S. Appl. No. 17/848,759, dated Dec. 29, 2022, 7 pages.
Corrected Notice of Allowance for U.S. Appl. No. 17/848,759, dated Jan. 12, 2023, 4 pages.
Official Action for U.S. Appl. No. 17/854,422, dated Sep. 28, 2022, 7 pages.
Official Action for U.S. Appl. No. 17/854,422, dated Jan. 10, 2023, 6 pages.
Notice of Allowance for U.S. Appl. No. 17/854,422, dated Feb. 17, 2023, 7 pages.
Official Action for U.S. Appl. No. 18/087,545, dated May 24, 2023, 5 pages.
Notice of Allowance for U.S. Appl. No. 18/087,545, dated Jul. 26, 2023, 7 pages.
Official Action for U.S. Appl. No. 18/178,847, dated Jul. 13, 2023, 8 pages.
Notice of Allowance for U.S. Appl. No. 18/178,847, dated Aug. 8, 2023, 8 pages.
Official Action for U.S. Appl. No. 18/130,946, dated Jun. 30, 2023, 6 pages.
Notice of Allowance for U.S. Appl. No. 18/130,946, dated Aug. 1, 2023, 8 pages.
Official Action for U.S. Appl. No. 15/228,454, dated Sep. 23, 2016, 11 pages.
Notice of Allowance for U.S. Appl. No. 15/228,454, dated Jan. 23, 2017, 7 pages.
Official Action for U.S. Appl. No. 15/437,976, dated Mar. 29, 2017, 8 pages.
Notice of Allowance for U.S. Appl. No. 15/437,976, dated Jul. 12, 2017, 7 pages.
Official Action for U.S. Appl. No. 15/639,767, dated Aug. 14, 2017, 11 pages.
Official Action for U.S. Appl. No. 15/639,767, dated Sep. 27, 2018, 13 pages.
Notice of Allowance for U.S. Appl. No. 15/369,767, dated Feb. 15, 2019, 8 pages.
Official Action for U.S. Appl. No. 16/426,346, dated Aug. 2, 2019, 10 pages.
Official Action for U.S. Appl. No. 16/426,346, dated Jan. 13, 2020, 7 pages.
Notice of Allowance for U.S. Appl. No. 16/426,346, dated Mar. 25, 2020, 7 pages.
Official Action for U.S. Appl. No. 13/367,052, dated Jan. 16, 2014, 8 pages.
Notice of Allowance for U.S. Appl. No. 13/367,052, dated Feb. 24, 2014, 5 pages.
Official Action for U.S. Appl. No. 14/225,503, dated May 4, 2016, 6 pages.
Notice of Allowance for U.S. Appl. No. 14/225,503, dated Jul. 20, 2016, 5 pages.
Official Action for U.S. Appl. No. 14/752,192, dated Jul. 8, 2016, 8 pages.
Notice of Allowance for U.S. Appl. No. 14/752,192, dated Sep. 16, 2016, 5 pages.
Official Action for U.S. Appl. No. 15/378,425, dated May 15, 2019, 82 pages.
Official Action for U.S. Appl. No. 15/378,425, dated Oct. 2, 2019, 41 pages.
Official Action for U.S. Appl. No. 15/378,425, dated Jul. 15, 2020, 21 pages.
Official Action for U.S. Appl. No. 15/378,425, dated Nov. 10, 2020, 29 pages.
Official Action for U.S. Appl. No. 15/385,278, dated Oct. 30, 2017, 23 pages.
Official Action for U.S. Appl. No. 15/385,278, dated Apr. 13, 2018, 18 pages.
Notice of Allowance for U.S. Appl. No. 15/385,278, dated May 31, 2018, 10 pages.
Official Action for U.S. Appl. No. 16/136,950, dated Nov. 25, 2019, 11 pages.
Official Action for U.S. Appl. No. 16/136,950, dated Jan. 31, 2020, 8 pages.
Official Action for U.S. Appl. No. 16/884,772, dated Sep. 30, 2021, 8 pages.
Notice of Allowance for U.S. Appl. No. 16/884,772, dated Feb. 22, 2022, 7 pages.
Official Action for U.S. Appl. No. 15/384,716, dated Nov. 1, 2017, 31 pages.
Notice of Allowance for U.S. Appl. No. 15/384,716, dated Apr. 2, 2018, 9 pages.
Official Action for U.S. Appl. No. 15/983,250, dated Mar. 5, 2019, 23 pages.
Official Action for U.S. Appl. No. 15/983,250, dated May 24, 2019, 21 pages.
Official Action for U.S. Appl. No. 15/983,250, dated Jan. 14, 2020, 8 pages.
Notice of Allowance for U.S. Appl. No. 15/983,250, dated Feb. 14, 2020, 8 pages.
Official Action for U.S. Appl. No. 16/904,056, dated Dec. 6, 2021, 12 pages.
Official Action for U.S. Appl. No. 16/904,056, dated May 17, 2022, 11 pages.
Notice of Allowance for U.S. Appl. No. 16/904,056, dated Aug. 11, 2022, 8 pages.
Corrected Notice of Allowance for U.S. Appl. No. 16/904,056, dated Aug. 24, 2022, 6 pages.
Official Action for U.S. Appl. No. 18/103,768, dated Apr. 25, 2023, 5 pages.
Notice of Allowance for U.S. Appl. No. 18/103,768, dated Aug. 1, 2023, 7 pages.
Official Action for U.S. Appl. No. 18/143,399, dated Sep. 7, 2023, 8 pages.

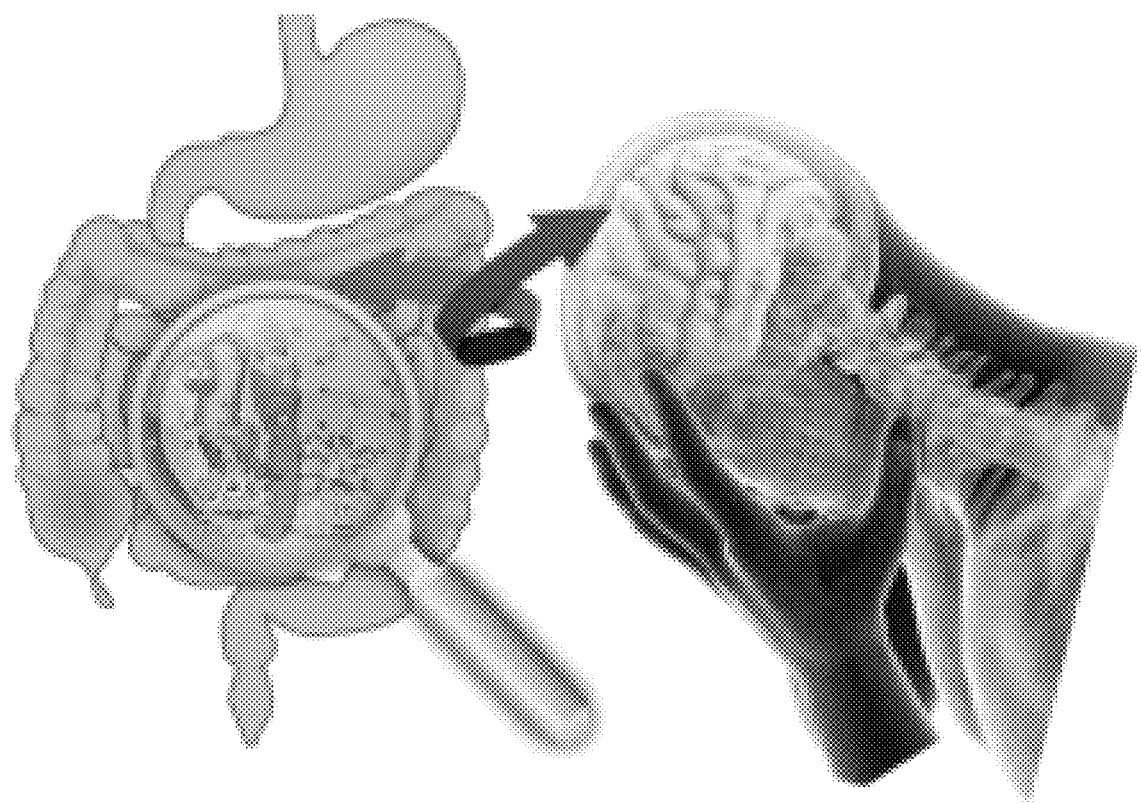

PROBIOTIC COMPOSITION AND METHOD FOR CONTROLLING EXCESS WEIGHT, OBESITY, NAFLD AND NASH

RELATED APPLICATIONS

This application is a continuation-in-part of U.S. patent application Ser. No. 18/232,433, filed Aug. 10, 2023, which is a continuation-in-part of U.S. patent application Ser. No. 18/143,399, filed May 4, 2023, which is a continuation-in-part application of U.S. patent application Ser. No. 17/893,384, filed Aug. 23, 2022, which is a continuation-in-part application of U.S. patent application Ser. No. 17/694,775, filed Mar. 15, 2022, which is a continuation-in-part of U.S. patent application Ser. No. 17/023,736, filed Sep. 17, 2020 (now U.S. Pat. No. 11,419,903, issued Aug. 23, 2022, which is a continuation-in-part of U.S. patent application Ser. No. 17/011,175, filed Sep. 3, 2020 (now U.S. Pat. No. 11,273,187, issued Mar. 15, 2022), which is a continuation-in-part of U.S. patent application Ser. No. 16/722,117, filed Dec. 20, 2019 (now U.S. Pat. No. 10,842,834, issued Nov. 24, 2020), which is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional Patent Application Ser. No. 62/275,341, filed on Jan. 6, 2016.

This application is a continuation-in-part of U.S. patent application Ser. No. 18/130,946, filed Apr. 5, 2023, which is continuation-in-part of U.S. patent application Ser. No. 18/178,847, filed Mar. 28, 2023, which is a continuation-in-part of U.S. patent application Ser. No. 18/087,545, filed Dec. 22, 2022, which is a continuation-in-part of U.S. patent application Ser. No. 17/854,422, filed Jun. 30, 2022 (now U.S. Pat. No. 11,672,835, issued Jun. 13, 2023), which is a continuation-in-part of U.S. patent application Ser. No. 17/848,759, filed Jun. 24, 2022 (now U.S. Pat. No. 11,642,382, issued May 9, 2023), which is a continuation-in-part of U.S. patent application Ser. No. 17/835,204 filed Jun. 8, 2022 (now U.S. Pat. No. 11,529,379, issued Dec. 20, 2022), which is a continuation-in-part of U.S. patent application Ser. No. 17/567,295 filed Jan. 3, 2022, which is a continuation-in-part of U.S. patent application Ser. No. 17/337,600, filed Jun. 3, 2021 (now U.S. Pat. No. 11,213,552, issued Jan. 4, 2022), which is a continuation-in-part of Ser. No. 17/027,953, filed on Sep. 22, 2020 (now U.S. Pat. No. 11,026,982, issued Jun. 8, 2021), which is a continuation-in-part of U.S. patent application Ser. No. 16/917,096, filed Jun. 30, 2020 (now U.S. Pat. No. 10,940,169, issued Mar. 9, 2021), which is a continuation-in-part of U.S. patent application Ser. No. 16/782,364, filed Feb. 5, 2020 (now U.S. Pat. No. 10,835,560, issued Nov. 17, 2020), which is a continuation-in-part of U.S. patent application Ser. No. 16/423,375, filed May 28, 2019 (now U.S. Pat. No. 10,555,976, issued Feb. 11, 2020), which is a continuation of U.S. patent application Ser. No. 16/160,336, filed Oct. 15, 2018 (now U.S. Pat. No. 10,314,866, issued Jun. 11, 2019), which is a continuation of U.S. patent application Ser. No. 15/403,823, filed Jan. 11, 2017 (now U.S. Pat. No. 10,111,913, issued Oct. 30, 2018), which is a non-provisional of U.S. Provisional Patent Application Ser. No. 62/296,186, filed on Feb. 17, 2016.

This application is a continuation-in-part of U.S. patent application Ser. No. 18/103,768, filed Jan. 31, 2023, which is a continuation-in-part of U.S. patent application Ser. No. 17/738,771, filed May 6, 2022, which is a continuation-in-part of U.S. patent application Ser. No. 16/904,056, filed Jun. 17, 2020 (now U.S. Pat. No. 11,523,934, issued Dec. 13, 2022), which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application is also a continuation-in-part of U.S. patent application Ser. No. 17/836,079, filed Jun. 9, 2022, which is a continuation-in-part of U.S. patent application Ser. No. 16/884,772 filed on May 27, 2020 (now U.S. Pat. No. 11,357,722, issued Jun. 14, 2022, which is a continuation-in-part of U.S. patent application Ser. No. 16/136,950, filed Sep. 20, 2018 (now U.S. Pat. No. 10,668,014, issued Jun. 2, 2020), which is a continuation of U.S. patent application Ser. No. 15/385,278, filed Dec. 20, 2016 (now U.S. Pat. No. 10,085,938, issued Dec. 2, 2018), which claims the benefit of U.S. Provisional Application Ser. No. 62/387,404, filed Dec. 24, 2015.

The present application is a continuation-in-part of U.S. patent application Ser. No. 17/543,992, filed Dec. 7, 2021, which is a continuation-in-part of U.S. patent application Ser. No. 16/804,361, filed Feb. 28, 2020 (now U.S. Pat. No. 11,191,665, issued Dec. 7, 2021), which is a continuation-in-part of U.S. patent application Ser. No. 16/020,433, filed Jun. 27, 2018 (now U.S. Pat. No. 10,583,033, issued Mar. 10, 2020), which is a continuation-in-part application of U.S. Ser. No. 15/342,642, filed Nov. 3, 2016 (now U.S. Pat. No. 10,010,568, issued Jul. 3, 2018), which seeks priority from U.S. Provisional Patent Application Ser. No. 62/260,906, filed Nov. 30, 2015.

This application is a continuation-in-part application of U.S. patent application Ser. No. 16/776,861, filed Jan. 30, 2020 (now U.S. Pat. No. 10,864,109, issued Dec. 15, 2020), which is a continuation of U.S. patent application Ser. No. 16/142,171, filed Sep. 26, 2018 (now U.S. Pat. No. 10,548,761, issued Feb. 4, 2020), which is a continuation-in-part of U.S. patent application Ser. No. 15/395,419, filed Dec. 2016 (now U.S. Pat. No. 10,086,018, issued Oct. 2, 2018), which is a non-provisional of U.S. Provisional Patent Application Ser. No. 62/274,550, filed on Jan. 4, 2016. This application is a continuation-in-part of U.S. patent application Ser. No. 16/426,346, filed May 30, 2019 (now U.S. Pat. No. 10,716,815, issued Jul. 21, 2020), which is a continuation of U.S. patent application Ser. No. 15/639,767, filed Jun. 30, 2017 (now issued U.S. Pat. No. 10,314,865, issuing Jun. 11, 2019), which is a continuation-in-part of U.S. patent application Ser. No. 15/437,976, filed Feb. 21, 2017 (now U.S. Pat. No. 9,730,967, issued Aug. 15, 2017), which is a continuation-in-part application of U.S. patent application Ser. No. 15/228,454, filed Aug. 4, 2016 (now U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016).

The present application is a continuation-in-part of U.S. patent application Ser. No. 17/543,992, filed Dec. 7, 2021, which is a continuation-in-part of U.S. patent application Ser. No. 16/804,361, filed Feb. 28, 2020 (now U.S. Pat. No. 11,191,665, issued Dec. 7, 2021), which is a continuation-in-part of U.S. patent application Ser. No. 16/020,433, filed Jun. 27, 2018 (now U.S. Pat. No. 10,583,033, issued Mar. 10, 2020), which is a continuation-in-part application of U.S. Ser. No. 15/342,642, filed Nov. 3, 2016 (now U.S. Pat.

No. 10,010,568, issued Jul. 3, 2018), which seeks priority from U.S. Provisional Patent Application Ser. No. 62/260,906, filed Nov. 30, 2015.

This application is a continuation-in-part application of U.S. patent application Ser. No. 16/037,053, filed Jul. 17, 2018.

This application is also a continuation-in-part of U.S. patent application Ser. No. 14/752,192 filed on Jun. 26, 2015 (now U.S. Pat. No. 9,549,842, issued Jan. 24, 2017).

The entire disclosure of the prior applications are considered to be part of the disclosure of the accompanying application and are hereby incorporated by reference.

FIELD OF THE INVENTION

The present invention relates to particular bacterial formulations for use as a medicament, in particular for preventing or controlling excess weight, obesity, cardiometabolic diseases and inflammatory bowel diseases, NAFLD and NASH. Embodiments of the present invention are directed to probiotic compositions and methods for controlling excess weight, obesity, NAFLD and NASH.

BACKGROUND OF THE INVENTION

In both developed and developing countries the chronic diseases caused by excess weight and obesity now affect all populations. A large part of the world's population now suffer from cardiometabolic diseases, such as diabetes and cardiovascular diseases, as well as certain cancers, neurodegenerative diseases and inflammatory bowel diseases. With the aging of the world's population, the ability to manage these chronic pathologies is presenting an immense problem on public health spending, which is becoming unbearable. The problems caused by excess weight and obesity, while in many cases attributed to one's genetics, is also associated with an individual's microbiome, which plays an important role in many chronic diseases, particularly obesity and cardiometabolic diseases. In particular, it has been found that dysbiosis of one's microbiome can lead to an increase in the absorption and storage of energy in the form of fat.

While every individual has their own microbiome, there are bacterial species common to many individuals. In particular, it is known that over 85% of the bacterial species are common between Europe, the United States and Japan.

The human gut is perhaps one of the most complex networks in the body and is colonized by trillions of microorganisms including bacteria, archaea, fungi, protists, and viruses, among which bacteria are the major inhabitants. Hepatocellular carcinoma (HCC) is one of the most common malignancies in the world. Gut microbiota has been demonstrated to play a critical role in liver inflammation, chronic fibrosis, liver cirrhosis, and HCC development through the gut-liver axis. Gut microbial dysbiosis accompanies the progression of alcoholic liver disease, non-alcoholic fatty liver disease and liver cirrhosis, and promotes HCC progression. Microbial dysbiosis contributes to cancer susceptibility via multiple pathways. The microbiota and its associated metabolites are closely related to carcinogenesis by inducing inflammation and immune dysregulation, leading to genetic instability, as well as interfering with the pharmacodynamics of anticancer agents. Chronic inflammation promotes tumor progression and accelerates tissue invasion and metastasis. The generation of inflammation-associated factors can also inactivate tumor-suppressor genes (e.g., P53 mutation). The hepatic environment is greatly influenced by the pathogens or metabolites produced by the microbiota and transported in the GI tract through the hepatic portal venous system. The liver exerts an essential effect on the host microbial community by filtering the blood stream as well as by metabolizing and neutralizing toxins derived from intestinal microbes. NAFLD is considered to be a major risk factor for HCC.

Obesity is a multifactorial disorder which is the result of a long-term imbalance between energy intake and expenditure and is influenced by genetic and environmental factors. Obesity is characterized by insulin resistance and chronic low-grade inflammation. Obesity increases the risk of developing and exacerbating a cluster of chronic metabolic disorders such as type 2 diabetes (T2DM), non-alcoholic fatty liver disease (NAFLD), hypertension, atherosclerosis, dyslipidemia and cardiovascular disease with the prevalence of metabolic comorbidities increasing in-line with increasing BMI. Obesity also increases the risk of developing serious and potentially life-threatening diseases such as allergies and asthma, osteoarthritis, gallbladder disease and Non-alcoholic steatohepatitis (NASH), a condition in which fat builds up in the liver, resulting in cirrhosis. Individuals with obesity, insulin resistance, and dyslipidemia are at the greatest risk of developing NAFLD.

NAFLD is the new pandemic of the twenty-first century, co-existing with obesity. Fatty liver is caused by an abnormality in liver metabolism that results in the accumulation of fat. It can be seen as a consequence of metabolic deregulation associated with energy surplus and exceeded reservoir ability of adipose tissue to store fat/energy. NAFLD is strongly associated with obesity, insulin resistance (IR)/type 2 diabetes mellitus (T2DM) and the metabolic syndrome. Obesity, particularly central obesity, is highly predictive of hepatic steatosis and disease progression, being directly proportional to the increase of body mass index (BMI). More than two thirds of patients with type-2 diabetes have NAFLD.

NAFLD is also associated with increased overall mortality and cardiovascular mortality. It is increasing worldwide, paralleling the obesity pandemic. It has been estimated that about one billion individuals worldwide have NAFLD. In the Western and in the Asian world, one third of the population is affected. NAFLD is presently the third cause of liver transplantation in the United States and is increasing at a rate such that it will be the first cause in the next few years.

NAFLD is the most common liver complication of irritable bowel syndrome and also affects people with ulcerative colitis and Crohn's disease. NAFLD has become the leading cause of chronic liver diseases worldwide, causing considerable liver-related mortality and morbidity. During the past decade, it has also become increasingly evident that NAFLD is a multisystem disease that affects many extra-hepatic organ systems, including the heart and the vascular system.

Non-alcoholic fatty liver disease is a condition ranging from benign lipid accumulation in the liver (steatosis) to steatosis combined with inflammation. The latter is referred to as non-alcoholic steatohepatitis (NASH). NASH is viewed as the hepatic component of metabolic syndrome. Estimates from the USA are that 5.7% to 17% of all adults have NASH, while 17% to 33% of Americans have NAFLD. As obesity and insulin resistance reach epidemic proportions in industrialized countries, the prevalence of both NAFLD and NASH is increasing and is therefore considered to be a major health hazard. Steatosis alone is considered a relatively benign condition for the liver itself and is also a reversible condition. However, the transition towards NASH represents a key step in the pathogenesis, as it sets the stage for further damage to the liver, such as fibrosis, cirrhosis and liver cancer. While the mechanisms leading to steatosis are well described, little is known about the actual risk factors that drive hepatic inflammation during the progression to NASH. Consequently, therapeutic options are poor.

The evolution of NAFLD has been postulated to involve lipid accumulation in the hepatocytes, followed by oxidative stress and inflammation, which can then lead to NASH. The initial metabolic stress generated by lipid accumulation in the hepatocytes triggers multiple cell stress pathways, including endoplasmic reticulum stress, mitochondrial dysfunction, oxidative stress (generation of reactive oxygen species), apoptosis and even necrosis. The generated hepatocellular injury leads to the release of signals that recruit and activate a variety of immune cells producing an inflammatory response. Such events activate hepatic stellate cells inducing an increase of collagen deposition resulting in fibrosis and eventually progress to cirrhosis and hepatocellular carcinoma.

The intestinal epithelium is the layer of cells that forms the luminal surface of the small and large intestines of the gastrointestinal (GI) tract, and represents the largest interface between the external environment and the internal milieu. The intestinal epithelium has two important functions: absorbing nutrients and providing a barrier against harmful environmental substances such as bacteria, viruses, toxins, and food allergens. The barrier properties of the intestinal epithelium are regulated by specialized plasma membrane structures known as tight junctions. Alterations in tight junctions can result in disruptions of the intestinal barrier functions and increased intestinal permeability. An intact intestinal barrier prevents the permeation of pathogens, antigens, endotoxins, and other proinflammatory substances into the body, whereas intestinal disintegrity allows their entry, which may trigger or exacerbate local or systemic inflammatory disease.

The number one cause of death in patients with NAFLD is cardiovascular disease, followed by malignancies and then liver disease. Despite huge amounts of money spent on investigating its origins and prevention, there is presently no effective treatment for NAFLD. At present, individuals diagnosed with NAFLD are treated by focusing on diet and exercise, in order to lose weight. Weight loss of 5% or more of body weight results in a NAFLD remission rate of 75%. In addition, recommendations are to have cholesterol intake lowered to 200 mg per day, whole grains emphasized and high fructose corn syrup avoided. Higher fructose consumption, in the form of soft drinks, has been associated with NAFLD as it is believed to promote bacterial overgrowth and hence increases the load of endotoxin that reaches the liver. Some studies have shown a possible beneficial effect in NAFLD for very mild alcohol consumption. Coffee has also been shown to have a protective effect in terms of metabolic control and NAFLD development and progression. The effect of lipid lowering agents in NAFLD is still not completely understood, though some studies have suggested a mild benefit in the use of statins. The accumulation of specific lipid intermediates, including DAG, acyl-CoA, and ceramide is thought to drive the progression of NAFLD in humans.

Existing treatments for NAFLD demonstrate various deficiencies. For example, available drugs such as vitamin E, pioglitazone, and pentoxifylline have borderline efficacy, but are limited by potential side-effects and toxicities, and do not improve liver fibrosis. Weight gain is common in patients taking thiazolidinediones, and these drugs can cause fluid retention and precipitate congestive heart failure. Rosiglitazone use is also associated with increased risk of myocardial infarction.

A genetic link to NAFLD has been studied but has not been found. NAFLD is more frequent in East Asian Indians, followed by Hispanics, Asians, Caucasians and less frequent in African Americans. While such racial disparities are not fully understood, it is known that African Americans have lower fructose absorption rates than Hispanics, and fructose is considered an important driver of liver steatogenesis.

The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity.

Long-chain-length hydrophobic acyl residues play a vital role in a multitude of essential biological structures and processes. Amongst other functions, they build the inner hydrophobic layers of biological membranes, are converted to intracellular storage compounds, and are used to modify protein properties or function as membrane anchors. Metabolic syndrome is an ever-increasing health problem among the world's population. It is a group of intertwined maladies that includes obesity, hypertriglyceridemia, hypertension, nonalcoholic fatty liver disease and diabetes mellitus type II (T2D).

There is a long-felt but unsolved need for an effective treatment for excess weight, obesity, NAFLD and NASH and the present invention is directed to a solution for these chronic and expanding conditions and diseases.

SUMMARY OF THE INVENTION

Various embodiments of the present invention are directed to a method and system for modulating an individual's microbiome in a manner such that individuals who are overweight, obese and/or suffer from cardiometabolic diseases and/or inflammatory bowel diseases are able to reduce the incidence of chronic conditions and diseases associated therewith. Certain embodiments are directed to a method and bacterial formulations for reducing the likelihood of developing NAFLD and NASH.

Various embodiments of the present invention are directed to the manipulation of gut microbiota by probiotics as a therapeutic tool to help ameliorate obesity and improve metabolic health. In various embodiments of the present invention, species of bacteria are identified that have an influence on weight loss by their increase in the microbiome, including various bacterial formulations and compositions that include one or more of the following: *Akkermansia muciniphila, Methanobrevibacter smithii, Faecalibacterium prausnitzii, Bifidobacterium longum, Roseburia intestinalis, Eubacterium* rectale and *Christenella minuta*.

In reducing the incidence of a common disease associated with obesity, diabetes, one aspect of various embodiments of the present invention involves a focus on combatting the significant decline in Clostridiales, *Roseburia intestinalis* and *Faecalibacterium pransnitzii*, and the increase of Bacteriodetes in those suffering from diabetes.

Still other embodiments of the present invention are directed to modulating an individual's microbiome in a manner such that individuals who are overweight, obese and/or suffer from cardiometabolic diseases and/or inflammatory bowel diseases are able to reduce the incidence of chronic conditions and diseases associated therewith.

One aspect of certain embodiments of the present invention relates to the use of various *Lactobacillus* species to reduce LDL, cholesterol, and triglycerides to cause an improvement and amelioration of inflammation and steatosis. The present inventors believe that particular modulation of the gut microbiome, including the establishment and maintenance of certain beneficial bacteria, including *Lactobacillus, Bifidobacterium*, and certain *Streptococcus* species, forms the basis of a treatment of NAFLD, as well as NASH, and in particular, the use of particular species that have been modified via a CRISPR system. Nonalcoholic steatohepatitis (NASH) is a more advanced form of NAFLD where liver injury has occurred, and can lead to liver failure, portal hypertension, hepatocarcinoma and cirrhosis. Even without significant changes in BMI, glucose, or LDL2, probiotic use is believed to significantly decrease ALT, AST, total cholesterol, HDL, and TNF-$\alpha$1.

Thus, in various embodiments of the present invention, the employment of particular probiotics as described herein, provides a treatment for NAFLD that shows improvements in intestinal dysbiosis, leading to decreasing intestinal permeability, endotoxemia and subsequent inflammation.

The most frequent cause which leads to obesity is a disbalance between energy intake and energy expenditure. The gut microbiota contributes to host metabolism. Gut microbiota not only influence absorption and disposal of nutrients to the liver, but also can lead to the development of "metabolic endotoxemia" and activation of TLR ligands, which can stimulate liver cells to produce proinflammatory cytokines, thereby initiating inflammation and fibrogenesis, which characterize NASH. Another possible molecular mechanism implicated in NAFLD development is the alteration in LPS-endocannabinoid (eCB) system regulatory loops and bile acid metabolism. Thus, certain embodiments of the present invention are directed to the modification of intestinal bacterial flora by specific probiotics to achieve a therapeutic approach for the treatment of NAFLD.

One strategy for NAFLD treatment encompassed by the present invention relates to a treatment for obesity that involves manipulation of an individual's gut microbiota. Thus, modulation of gut microbiota by probiotic treatment or dietary intervention provides beneficial effects with respect to body weight, influence on glucose and fat metabolism, insulin sensitivity and reduction in chronic systemic inflammation, all of which can impact the status of NAFLD. Probiotic positive effects on host metabolism are specifically directed to beneficial levels of *Lactobacillus* and/or *Bifidobacterium* strains. For example, employment of *Saccharomyces cerevisiae* var. *boulardii, Enterobacter halii* or *Akkermansia muciniphila* are used to achieve beneficial effects for obesity and NAFLD. In certain embodiments, because obstructive sleep apnea and attendant fatigue are common in patients with NAFLD, one aspect of the present invention relates to the use of "no-snore strips" as described herein (and in more extensive pending patent applications incorporated herein by this reference, e.g. U.S. Pat. No. 9,445,936) such that use of such strips can beneficially modify not only the populations of oral bacteria, but also snoring patterns, thus providing those suffering from NAFLD with a way to manage such condition to permit them to address fatigue issues and to thus sleep better, exercise more, etc.

Gut bacteria alter the way individuals store fat, how levels of glucose are balanced in the blood, and how humans respond to hormones that make individuals feel hungry or full. Certain population mixes of microbes set the stage for NAFLD, obesity and diabetes. The gut community in lean people is diverse while obese people have a gut microbe community that is comparatively less diverse. Lean individuals, for example, tended to have a wider variety of Bacteroidetes, a population of varied microbes that specialize in breaking down bulky plant starches and fibers into shorter molecules that the body can use as a source of energy.

Probiotics have physiologic functions that contribute to the health of gut microbiota, can affect food intake and appetite, body weight and composition and metabolic functions through gastrointestinal pathways and the modulation of the gut bacterial community. Thus, in various embodiments of the present invention, probiotics are employed, e.g. (*Enterococcus faecium, Streptococcus thermophilus L. acidophilus, Bifidobacterium longum, L. plantarum* and/or *B. lactis*) to significantly reduce total serum cholesterol and LDL cholesterol and to improve the LDL:HDL cholesterol ratio. In particular embodiments, a CRISPR-Cas system (Clustered Regularly Interspaced Short Palindromic Repeats-CRISPR-associated) is employed to alter one or more of these bacteria to modify various virulence factors associated with bacteria so that beneficial populations of bacteria inhabit an individual's oral and/or gut microbiome.

Various embodiments of the present invention relate to a composition capable of increasing the level of anti-oxidized low-density-lipoprotein (oxLDL) antibodies in vivo for use in the treatment or prevention of NASH. OxLDL is an immunogenic molecule that stimulates the induction of anti-oxLDL antibodies. Phosphorylcholine, a component of *Streptococcus pneumoniae*, is a major antigen in oxLDL, which is recognized by anti-oxLDL antibodies that have protective properties. One embodiment relates to the expression of OxLDL in bacteria via employment of a CRISPR-Cas system to insert genes for OxLDL such that such modified bacteria produce OxLDL to therefore stimulate the induction of anti-oxLDL antibodies, thus providing the protective effects of such antibodies. Using the present invention, fibrosis can be decreased or prevented by the production and administration of anti-oxLDL antibodies to avoid inflammation of the liver and to therefore treat NASH and NAFLD. While antibodies against oxLDL are known in the art, various embodiments of the present invention relate to a new medical use of such antibodies, as well as to methods and systems that modify gut bacteria to enhance the production of such antibodies. In other words, various embodiments of the invention relate to a composition comprising antibodies against oxLDL for use in the treatment or prevention of hepatic inflammation or more in particular the treatment or prevention of NASH, and/or the use of oxLDL antibodies for the preparation of a medicament for the treatment or prevention of hepatic inflammation and in the treatment of NASH. In certain embodiments, a method of treatment or prevention of hepatic inflammation is provided where oxLDL antibody levels are increased by modification of particular bacteria using a Clustered Regularly Interspaced Short Palindromic Repeats-CRISPR-associated system (CRISPR-Cas) or Clustered Regularly Interspaced Short Palindromic Repeats from *Prevotella* and *Francisella* 1 (CRISPR/Cpf1) system so that the bacteria is able to produce desired levels of oxLDL anti-bodies.

In other embodiments, the methods and systems disclosed herein are directed to modifying the gut microbiota of an individual to ameliorate the progression of NAFLD, including reducing liver aminotransferases, total-cholesterol, TNF-α and improving insulin resistance in individuals with NAFLD. In certain embodiments, NAFLD is thus treated by modulation of the gut microbiota. Effective treatments include employing a method of populating a subject's gastrointestinal tract with a diverse and useful selection of microbiota in order to alter a dysbiosis. Various aspects and embodiments of the invention are directed to methods and compositions for modulation of NAFLD of an individual's gut microbiome by using bacteria that have been treated with a CRISPR-Cas or CRISPR-Cpf1 system to reverse antibiotic resistance or to render ineffective certain virulence factors in pathogenic bacterial cell, as well as modifying gut bacteria in a manner to make them "better" in various ways, including an ability to outcompete other undesired bacteria. Other various embodiments of the present invention relate to the employment of engineered autonomously distributed circuits containing programmable nucleases (e.g. "programmable nuclease circuits") that are delivered to microbial organisms in vivo to modulate the expression of certain antibiotic resistant and virulence factors of particular microbial organisms. Some embodiments employ the Type II CRISPR-Cas (Clustered Regularly Interspaced Short Palindromic Repeats-CRISPR-associated) system of *Streptococcus pyogenes* to reverse antibiotic resistance in a wide range of microbial organisms. In certain embodiments, the CRISPR-Cas system is used to weaken resistance of microbial pathogens to existing antibiotics. The use of the CRISPR-Cas system may be viewed as a paradigm shift in combating pathogens because it enables autonomous and distributed neutralization of disease at the gene level. Various aspects of the present disclosure provide methods that comprise modifying bacterial cells to target a gene or nucleotide sequence of interest, and in particular, genes involved in the storage of fat. Such modified bacterial cells include an engineered autonomously distributed circuit having at least one nucleic acid encoding a programmable nuclease that targets a gene or nucleotide sequence directed to fat metabolism.

While there are medications approved for treating diseases and conditions associated with NAFLD, there are currently no medications specifically approved for the treatment of NAFLD itself. Treatment protocols have instead been focused upon the associated conditions, such as the metabolic syndrome. Conventional treatment of NAFLD includes weight loss, restricting dietary fat, administration of medications employed in the treatment of an associated condition and administration of medications employed in the treatment of hyperlipidemia. Many medications employed to treat conditions associated with NAFLD are hepatotoxic.

Various embodiments of the present invention are directed to a method for treating NAFLD in a subject in need thereof that includes administering a composition including a therapeutically effective amount of *Prevotella*, and more preferably *Prevotella* that has been modified, e.g. by CRISPR-Cas, in a manner that reduces the effect of at least one of the virulence factors of such bacteria. Other embodiments involve the employment of bacteria of the *Bacteroides* family that have been modified to reduce the amount of a ligand-activated transcription factor.

Dysbiosis in a person's gut has a significant role in the pathogenesis of human NAFLD/NASH. In various embodiments of the present invention, administration of probiotics, as well as associated fiber diets to support such bacteria, is involved, in some embodiments employing *Bifidobacterium* and *Lactobacillus* strains. Control of the bacterial flora lowers proinflammatory cytokine production (tumor necrosis factor-α, interleukin-6, interferon-γ) via down-regulation of the nuclear factor kappa B, and decreases oxidative stress. Probiotics can reduce the urease activity of bacterial microflora, decrease fecal pH value and reduces amino-acid fermentation and ammonia adsorption; reduce aminotransferases, and improve the lipid status in NAFLD patients. Each of these may be modified via CRISPR-Cas systems employed to alternative characteristics of an individual's microbiome.

Microbiome research in liver disease has evolved recently as an exciting new field Prebiotics encompass products that promote the growth of beneficial intestinal microbiota. Probiotics include live microbial strains in predefined quantities. Both prebiotics and the use of probiotics is involved in the various embodiments of the invention as herein described. The present invention is directed in various embodiments directed to ways to modify the microbiota to treat hepatic steatosis, liver inflammation, fibrosis, and developing and advanced liver disease. The purposeful manipulation of the gut microbiota is done to address various liver diseases at both early and late disease stages.

More than 90% of the adult microbiome is composed of species belonging to four bacterial phyla: Firmicutes, Bacteroidetes, Actinobacteria, and Proteobacteria. Differences exist, however, with respect to different individuals as well as in different habitats. For example, Firmicutes are the major species in the intestine, vagina, skin, and oral cavity, while Actinobacteria and Proteobacteria are more dominant in the oral cavity, skin, and nasal cavity. The enterotype is a classification of the microbiome, with the gut microbiome being classified into three enterotypes. Each enterotype includes a dominant species selected from the group consisting of: *Bacteroides, Prevotella*, and *Ruminococcus*, with enterotypes being unrelated to race, residential region, or diet.

The prevalence of nonalcoholic fatty liver disease (NAFLD) overall is lower in Asia than in Western countries. Urban areas in India and other parts of Asia that have adapted a 'Western' diet report prevalence rates for NAFLD and NASH of 10-24 and 3-4%, respectively, which is similar to their prevalence rates in the West. In addition, the prevalence of NAFLD in an obese population was similarly high in Asia and Western countries. Thus, differences in NAFLD etiology and prevalence are more closely related to dietary patterns than geographic differences.

It is believed that commensal microbiota protect against biliary injury and liver fibrosis. The present inventor believes that there is a significant association of fatty liver with *H. pylori* infection. Thus, various embodiments involve the modification of an individual's microbiome, including *H. pylori* in one's stomach, to combat NAFLD and NASH. Thus use of CRISPR-Cas to render *H. pylori* more susceptible to particular antibiotics is one way in which such modification may be achieved.

NAFLD is a complex disease and a treatment targeting one pathological process often also causes changes in other pathways. Prebiotics represent a specific type of dietary fiber that when fermented, mediate measurable changes within the gut microbiota composition, usually causing an increase in the relative abundance of bacteria thought of as beneficial, such as bifidobacteria or certain butyrate producers. Prebiotics are usually non-digestible carbohydrates, oligosaccharides or short polysaccharides, including inulin, oligofructose, galactofructose, galacto-oligosaccharides and xylo-oligosaccharides, all leading to increasing the relative abundance of bifidobacteria and lactobacilli. The gut of individuals with various maladies, including obesity, harbor bacteria in their gut that establishes an inflammation-associated microbiome, often providing a lower potential for butyrate production and reduced bacterial diversity. Thus, one objective of the present invention is to alter the microbiome of such individuals to increase bacterial diversity in their gut and to increase levels of butyrate production. Patients with NAFLD have small intestinal bacterial overgrowth and increased intestinal permeability. Thus, altering the microbiome of such individuals is achieved to counter the progression of NAFLD. In certain embodiments, one objective is to increase the proportion of Ruminococcaceae in a person's microbiome and to also reduce the proportion of *Escherichia*, e.g. by modifying *Escherichia* via CRISPR-Cas to make it less viable than it otherwise would be.

Probiotics can reduce liver aminotransferases, total cholesterol, tumor necrosis factor α and improve insulin resistance in patients with NAFLD. Similarly, treatment of other diseases in the gut, like inflammatory bowel disease (IBD) is implicated with respect to modification of the gut microbiome. The concept of an altered gut microbiota or dysbiosis is possibly the most significant development in IBD and NAFLD research in the past decade. A definitive change of the normal gut microbiota with a breakdown of host-microbial mutualism is believed to be the defining event in IBD and NAFLD development.

In other embodiments, one objective is to increase the levels of *Lactobacillus, Leuconostoc, Lactococcus, Pediococcus* and Firmicutes in an individual's gut microbiome, while reducing the levels of Bacteroidetes and *Akkermansia* spp. In certain other embodiments, one objective is to increase the levels of *Prevotella* and *Roseburia* (a butyrate-producer) in a person's gut microbiome, and especially the colon microbiome. Other embodiments focus on increasing the levels of *Bacteroides* in the person's gut and decreasing the levels of *Escherichia*, Lachnospiraceae and Megasphaera.

Periodontal disease is a chronic infectious disease of the tissues surrounding the teeth that result in tooth loss. Several reports have indicated that periodontal infection is related to NAFLD. Both NAFLD and periodontal disease are chronic inflammatory conditions that are known as 'silent diseases'. Therefore, both conditions need to be detected early and treated under collaborative medical and dental care in order to prevent progression to NASH. The prevalence of NAFLD in the American general adult population is 10%-40% and that of NASH is approximately 2%-5%. One aspect of the present invention is directed to the relationship between periodontal pathogens, e.g. composed of *P. gingivalis*, and the severity of NAFLD. The eradication of periodontal pathogens, such as *P. gingivalis* infection, is believed to have a beneficial effect upon NASH.

Certain embodiments of the present invention are directed to a method for treating non-alcoholic fatty liver disease by providing to an individual in need thereof an effective amount of a composition comprising modified *L. reuteri* bacteria, preferably using CRISPR-Cas and/or Cpf1 systems, to provide such bacteria in a manner so that they have the ability to survive the conditions in the duodenum or jejunum of the small intestine. Other embodiments involve a method for treating non-alcoholic fatty liver disease involving establishing in the gut of an individual a population of beneficial bacteria selected from the group consisting of *Lactobacillus, Bifidobacterium*, and *Streptococcus* species and administering at least 6 grams per day of fiber to the individual to maintain the beneficial bacteria in the gut of the individual. Still other embodiments are directed to a method for treating non-alcoholic fatty liver disease by increasing oxLDL antibody levels in an individual by modifying bacteria, preferably using a CRISPR-Cas or Cpf1 system, so that the bacteria is able to produce desired levels of oxLDL. Yet other methods involve the modulation of NAFLD of an individual's gut microbiome by using beneficial bacteria, e.g. such as one or more of bacteria from one or more of the phylas: Firmicutes, Bacteroidetes, Actinobacteria, and Proteobacteria, preferably treated with a CRISPR-Cas or CRISPR-Cpf1 system to reverse antibiotic resistance or to render ineffective certain virulence factors in pathogenic bacterial cells. In other embodiments, an individual is administered a therapeutically effective amount of *Prevotella*, and more preferably *Prevotella* that has been modified in a manner that reduces the effect of at least one of the virulence factors of such bacteria. Certain embodiments are directed to a method for treating non-alcoholic fatty liver disease involving the modifying of bacteria of the *Bacteroides* family so that they produce reduced amounts of a ligand-activated transcription factor as compared to non-modified bacteria. In preferred embodiments, probiotics are further provided to feed such bacteria, with the result being improvements in levels of density lipoprotein, and tumor necrosis factor-α.

Certain aspects of the present invention are directed towards the use of microbes as therapeutics for management of one of controlling excess weight, obesity, NAFLD and NASH using bacterial formulations that include probiotic bacterial strains as protective agents against the development of such conditions and diseases. In certain embodiments, a combination of *Lactocaseibacillus rhamnosus, L. plantarum* and *L. casei* are employed to provide preventive effects of dampening the disruption of tight junction proteins and to ameliorate barrier function issues.

In certain embodiments, an increase of indoles in an individual's gut is employed to advance the health of the individual. In particular embodiments, indole-3-lactic acid and indole-3-acateldehyde levels are increased to at least about 1 mM to reduce epithelial permeability and to increase barrier function. While not bound by theory, this is believed to be accomplished by the upregulation of genes responsible for tight junction and cytoskeleton assembly as indoles inhibit inflammatory pathways in an individual's liver. In preferred embodiments, bacteria formulations derived from the *Bibidobacterium* genus are employed as it is believed to be a better inducer of GLP-1 than the *Lactobacillus* genus. To combat obesity, indole metabolites are increased in the gut of individuals to achieve hepatoprotective effects, for example, by the oral administration of indoles in an amount at least 40 mg/kg for at least three weeks.

It is further believed that indole stimulates AhR and thus, certain embodiments are directed to providing to an individual's gut microbiome indole high-producing bacterial strains to increase liver health.

Still other embodiments are directed to the use of bacterial strains with prophylactic properties against NAFLD, namely, using liver-health promoting bacteria, e.g., those bacteria that are able to strengthen the gut barrier, boost GLP-1 secretion, affect organoid transcriptomic profile, and inhibit hepatic lipogenesis, thus improving the integrity of the gut lining. Preferably, *Bifidobacterium* strains are used due to their production of indole-3-lactic acid and indole-3-aceadehyde, which are metabolites with recognized beneficial physiological actions, including inhibition of hepatic lipogenesis.

In certain embodiments, the bacteria *B. longum* is employed either alone or more preferably in combination with other species of bacteria (e.g. *F. prausnitzii, Akkermansia; Coprcococcus; Bifidobacterium breve; Roseburia*) to benefit a person's digestive tract and gut microbiome. While not bound by theory, it is believed that *B. longum* aids in inhibiting the production of certain toxigenic and/or immunogenic peptides that are involved in various diseases, such as celiac disease. While not bound by theory, NAFLD is associated with celiac disease and thus, the treatment of one condition can beneficially treat the other. Oral administration of bacterial formulations that contain *B. longum* form aspects of certain embodiments where *B. longum* benefits an individual's gut microbiome by interfering with the digestion of gluten. In one embodiment, a bacterial formulation, preferably orally administered, comprises at least one of *Bifidobacterium breve* and *B. longum* to decrease the severity of diarrhea, alleviate celiac disease, and reduce undesired aspects of neurological disorders and mental disorders. Thus, in one embodiment, a method for reducing the likelihood of developing non-alcoholic fatty liver disease involves providing a bacterial formulation through oral administration that comprises both *Bifidobacterium breve* and *B. longum* in an amount sufficient to achieve at least one of the following: decrease the severity of diarrhea; and reduce the symptoms of celiac disease.

As described herein the growth of these and other bacteria are fostered while other pathogenic bacteria are selectively killed or their growth retarded. The beneficial bacterial formulations as set forth herein not only influence absorption and disposal of nutrients to the liver, but also can interrupt the development of "metabolic endotoxemia" and activation of TLR ligands, which can stimulate liver cells to produce proinflammatory cytokines, thereby initiating inflammation and fibrogenesis, which characterize NASH. Thus, certain embodiments of the present invention are directed to the modification of intestinal bacterial flora by specific probiotics to achieve a therapeutic approach for the treatment of NAFLD and NASH by the modulation of bile acid metabolism. The employment of particular probiotics as described herein provides a treatment for NAFLD that shows improvements in intestinal dysbiosis, leading to decreasing intestinal permeability, endotoxemia and subsequent inflammation. Probiotic positive effects on host metabolism are specifically directed to beneficial levels of *Lactobacillus* and/or *Bifidobacterium* strains, *Saccharomyces cerevisiae* var. *boulardii, Enterobacter halii* and *Akkermansia muciniphila*, with such bacterial formulations (preferably at least three of the above species in a formulation) used to achieve beneficial effects for obesity and NAFLD. Because gut bacteria alter the way individuals store fat, with lean individuals having a more diverse gut microbe community than obese individuals, one aspect of certain embodiments is directed to increasing the variety of Bacteroidetes so as to increase the breaking down of bulky plant starches and fibers into shorter molecules that the body can use as a source of energy. In various embodiments of the present invention, probiotics that include at least two of the following are employed: *Enterococcus faecium, Streptococcus thermophilus, L. acidophilus, Bifidobacterium longum, L. plantarum* and *B. lactis*, so as to reduce total serum cholesterol and LDL cholesterol and to improve the LDL:HDL cholesterol ratio in an individual.

Bacterial metabolites, such as short-chain fatty acids (SCFAs) and indoles, exert beneficial effects on an individual. The production by gut microbes of acetate, propionate, and butyrate result from the fermentation of non-digestible dietary fibers, whereas indoles are generated by microbial catabolism of tryptophan. Indoles act as signaling molecules, for example, through the activation of aryl hydrocarbon receptor (AhR). Certain aspects of the present invention are directed to increasing the levels of SCFAs to avoid and treat NAFLD. Indoles, and specifically, indole-3-acetic acid, is preferably administered to alleviate NAFLD. Increasing intestinal AhR activation is one objective of certain embodiments. While not bound by theory, both SCFAs and indoles are believed to modulate the secretion of gut hormones, particularly glucargon-like peptide-1 (GLP-1), which controls glucose-dependent insulin secretion, β-cell mass, satiety sensation, and gastric emptying, and thus aspects of various embodiments are directed to administering a GLP-1 agonist treatment to achieve beneficial effects on hepatic inflammation, steatosis, and fibrosis by increasing circulating GLP-1. Various embodiments employ probiotic supplementation to provide a therapy that modulates intestinal epithelial integrity, gut hormone release and metabolite production. In certain, SCFAs are used to modulate oxidative stress and to enhance tight junction proteins between endothelial cells and intestinal epithelial cells, thereby providing a direct protective effect on both the stabilization and the recovery of the intestinal epithelial barrier.

Various embodiments of the present invention involve the modification of at least two, if not three separate microbiomes of a person to treat certain conditions. This particular aspect of the present invention, while simple in nature, is believed to have profound effects in avoiding undesired drug interactions that can complicate treatment regimens. By having different microbiomes of the same individual administer different desired compounds, drugs, factors, proteins, etc. to the person's body, the ability to separately control administration and amounts (as well as to address issues by killing bacteria in one but not the other microbiome) is rendered feasible as a way to administer, for example, desired cancer fighting agents to an individual.

Through coevolution of bacteria, archaea and fungi with the human host over thousands of years, a complex host-microbiome relationship emerged in which many functions, including metabolism and immune responses, became codependent. This coupling becomes evident when disruption in the microbiome composition, termed dysbiosis, is mirrored by the development of pathologies in the host. Among the most serious consequences of dysbiosis, is the development of cancer. Various embodiments of the present invention are directed to the field of Oncology, and in particular, embodiments directed to a method of ameliorating, treating, or preventing a malignancy in a human subject wherein the steps of the method assist or boost the immune system in eradicating cancerous cells. In certain embodiments, administration of beneficial bacteria to an individual's microbiome that have been modified so as to produce effective amounts of desired compositions, compounds, agents, e.g. tomatidine, p53 protein, etc., is employed to address cancerous conditions. In several embodiments, the administration of such beneficial bacteria and microbes to an individual's microbiome invokes either an active (or a passive) immune response to destroy, weaken or render less invasive certain cancerous cells, and preferably maintains muscle tissue to combat cancer cachexia. Various embodiments of the present invention involve the expression/production by microbes of an individual's microbiome of a phytochemical to enhance the lifespan and health of a human.

Preferably, the modified bacteria employed in the present invention are administered orally to a patient in order to deliver the therapeutic directly to the site of inflammation in the gut. Suppositories can also be employed for administration of particular bacteria that may be more difficult to deliver to a particular portion of a person's body, e.g. those that may be destroyed while passing through a person's stomach. The advantage of an oral, vaginal or rectal approach is that it avoids systemic administration of immunosuppressive drugs and delivers the therapeutic directly to the gastrointestinal tract. In certain embodiments, the viability and stability of such modified bacteria is enhanced to support the production of such microbes of desired agents/compounds, e.g. tomatidine, p53 protein, rapamycin, resveratrol, methylene blue, etc. and by doing so, a method is provided that reduces gut inflammation, enhances gut barrier function, and/or treats autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate is produced, which induces the differentiation of regulatory T cells in the gut and/or promotes the barrier function of colonic epithelial cells.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Use of such modified bacteria, especially those modified via CRISPR-Cas systems, provides a way to generate a desired therapeutic effect in a manner that lowers the safety issues associated with systemic exposure. Resveratrol is a polyphenolic phytoalexin found in grapes, berries, peanuts, and wines. Resveratrol has been viewed as an antioxidant, anti-inflammatory, anti-apoptotic, and anti-cancer agent. Moreover, it has been reported that resveratrol modulates mitochondrial function, redox biology, and dynamics in both in vitro and in vivo experimental models. Resveratrol also attenuates mitochondrial impairment induced by certain stressors. Resveratrol upregulates, for example, mitochondria-located antioxidant enzymes, decreasing the production of reactive species by these organelles. Resveratrol also triggers mitochondrial biogenesis, ameliorating the mitochondria-related bioenergetics status in mammalian cells. Brain cells (both neuronal and glial) are susceptible to mitochondrial dysfunction due to their high demand for adenosine triphosphate (ATP). Additionally, brain cells consume oxygen at very high rates, leading to a proportionally high mitochondrial production of reactive species. One aspect of various embodiments of the present invention is the maintenance of mitochondrial function in various cell types to address degenerative diseases, which involve mitochondrial impairment and increased generation of reactive species, leading, for example, to neuroinflammation and cell death. The mechanism by which resveratrol protects mitochondrial function and dynamics is not completely understood, but it is known that resveratrol is able to induce cytotoxicity depending on its dosage. Resveratrol produced by the microbiome of an individual can be employed to improve the dysregulation of the gut microbiota induced by a high-fat diet, as it will result in increasing the ratio of *Bacteroides*-to-Firmicutes and also increases the growth of *Lactobacillus acidophilus* and *Bifidobacterium* in humans. It is believed that resveratrol modifies the intracellular environment by changing the oxidizing milieu into a reducing milieu and upregulates intracellular glutathione, potentiating a signal transduction cascade that results in mitophagy, and thus paves the way to an anti-aging environment. Rapamycin was first discovered in Easter Island soil bacteria in the 1980s. It is known that rapamycin extends the life span of mice. The protein that rapamycin targets is a kinase called mTOR. This kinase plays a role in a variety of pathways. mTOR suppresses some senescent cells from secreting their cocktail of problematic molecules and mTOR plays a role in the positive effects of caloric restriction. But given the disparity of microbiome constituents between any two individuals, the present inventors contend that the manner by which to effectively address aging of any particular individual lies in taking advantage of the noted differences of each individual's microbiome to address the aging mechanisms involved.

Nonalcoholic fatty liver disease (NAFLD) is a risk factor for colorectal cancer. NAFLD is associated with a high incidence of CRC. Age is an important factor for CRC and the CRC incidence increases with age.

One aspect of the present invention is directed to therapeutic interventions in the microbiome directed against molecular entities, such as essential and antibiotic resistance genes to quorum sensing systems components used to control microbial networking behaviors, including the chemical communication and production of virulence factors. Various embodiments are focused on dietary interventions and microbial modification genetic tools to modify and/or eliminate pathogenic microorganisms and to control dysbiosis. Various embodiments of the present invention are also directed towards the modification of the human-microbiota ecosystem to promote health and to combat disease, including the modification and/or elimination of certain bacteria living in the human body. The determination of human microbiota and the analyses of the presence or absence of specific microbial species in accordance with particular diseases provides one of skill in the art with the ability to identify particular biomarkers and to target the same to treat GERD.

While phage therapy could potentially have beneficial impact on human microbiomes, host specificity greatly limits the types of bacteria that can be employed and the selection of a specific phage to use as a therapeutic agent requires in-depth knowledge of the pathogen causing a given disease. In the absence of such knowledge, some have suggested the use of a cocktail of different species of phages to broaden the range of action, but such a cocktail could have undesired negative effects on the microbial community. Thus, in preferred embodiments of the present invention, CRISPR systems are employed to effect desired microbial modifications. The relative simplicity of the mechanism of action and the peculiarities of Cas9 make the CRISPR/Cas9 system an ideal tool for a vast assortment of procedures, particularly for genomic editing.

In various embodiments of the present invention, various targets for intervention using CRISPR-Cas systems include the modification of bacteria resident in the human gut that are distinct from humans in various respects. For example, most bacteria synthesize thiamine de novo, whereas humans depend on dietary uptake. Methionine is not synthesized de novo in humans and must be supplied by diet. In contrast, most bacteria need to synthesize methionine to survive. There are a myriad of other orthologous gene groups conserved in both human and human commensal gut microflora that are not suitable targets for drug development. The majority of unique targets found in microbes' genomes are genes responsible for the metabolism of carbohydrates, amino acids, xenobiotics, methanogenesis, and the biosynthesis of vitamins and isoprenoids, and in particular for the purposes of various embodiments of the present invention, focus is directed to those genes that are non-homologous to those encompassed in human genome. A number of microbial genes and products, including bacteriocins, lysins, holins, restriction/modification endonuclease systems, and other virulence factors contribute to resistance to antibiotics. Thus, an alternative to killing or inhibiting growth of pathogenic bacteria is targeting these key regulatory systems. Other aspects of the present invention are directed to targeted changes in microbiota by the rational use of prebiotics and probiotics to abolish metabolic alterations associated with various maladies, including GERD, obesity, cancer, etc.

In particular embodiments, compounds such as halogenated furanones produced by many microbial species, mostly belonging to the proteobacteria, are employed to interfere with AHL and AI-2 QS pathways in Gram-negative and Gram-positive bacteria. It is believed that by interrupting normal systems of bacterial inter and intra quorum sensing, one may effectively modify bacterial cell-cell communication in a manner that prevents colonization by pathogenic bacteria.

In particular embodiments, probiotic microorganisms that possess resistance to low gastric pH and have the capacity to reach the intestines alive, are used to exert beneficial effects on the human body, preferably lactic acid-producing bacteria of the *Lactobacillus* and *Bifidobacterium* genera. Such microorganisms are preferably those modified using CRISPR-Cas to provide a population that can be more easily controlled and manipulated to maintain particular levels in an individual's microbiome. Specifically, some embodiments of the present invention include regulating the balance of intestinal microbiota by physically blocking the adhesion of pathogenic species onto epithelial cells, such blocking action directly mediated by means of increases in the production of a mucosal barrier by goblet epithelial cells and/or by regulating epithelial permeability by enhancing the formation of tight-junctions between cells. Use of CRISPR-Cas to modify or delete virulence factors of particular bacteria, such as adhesion abilities thereof, is employed in this fashion.

In various embodiments of the present invention, CRISPR/Cas9 is used to selectively deplete a given bacterial community of a particular harmful strain or species, or of particular virulence factors possessed by particular strains of bacteria. Thus, in certain embodiments, the identification of a harmful pathogen is performed, and CRISPR/Cas9 is then used to selectively deplete or modify that particular bacterial species from an individual's gut microbiota. The use of antibiotics is believed to increase the ability of bacteria to acquire drug resistance-encoding plasmids. Thus, the CRISPR/Cas9 system may be used to introduce specific mutations into essential, antibiotic resistance and virulence genes, as well as to directly modulate the expression of particular genes. For example, one can employ a Cas protein that lacks nuclease activity but retains a binding capacity so as to repress bacterial transcription by binding to promoter regions to effect the blocking of transcriptional initiation and/or elongation. CRISPR-Cas or Cpf1 systems may also be used to fuse regulatory domains in order to switch on/off the expression of specific genes. Thus, the present invention includes the engineering of commensal bacteria with improved properties using a CRISPR/Cas system to prevent and treat diseases. One of skill in the art will appreciate the steps required to affect the desired levels of target specificity and delivering efficiency.

Still other embodiments employ the modification of various beneficial bacteria so that they express certain compounds and substances, notably those substances found to be effective as an anti-*H. pylori* agent, such as those isolated from garlic and ginseng. Alliin, the main active molecule present in Garlic extract, is used to effect immune modulation. The use of dialkyl-thiosulfinate and/or propy thiosulfonate can be employed to improve disease resistance of a pathogen, with these compounds generated from the natural degradation of propiin, a molecule present in most *Allium* species, and more specifically onion, shallots or chives. Still other sulfur compounds may be employed to inhibit *H. pylori* colonization. Using CRISPR-Cas, one is able to modify resident bacteria to express the active ingredient in garlic found to be an effective killer of *H. pylori*. Such expressed compounds include those described above.

Similarly, another aspect of the present invention is to control *H. pylori* populations in an individual's stomach by a diet including kimchi. Other aspects are directed to the expression of kimchi genes by one or more bacterial species that reside in a human stomach. In a manner similar to the expression of certain genes derived from garlic, one is therefore able to control the population of *H. pylori* in a person's stomach. The use of CRISPR-Cas to insert genes into particular bacteria so as to facilitate the control of *H. pylori* is one aspect of certain embodiments, including the insertion of genes having the active agent contained in Korean kimchi and garlic. The incidence of gastric cancer is about 20 per 100,000 population (in Korea) and about 50 per 100,000 population (in Japan, where far less kimchi is eaten), demonstrating that kimchi is effective as a cancer preventative agent. Similarly, the expression of garlic related genes by one or more bacterial species that reside in a human stomach is another embodiment of the present invention. The use of garlic (as well as kimchi) to address GERD is considered to be a teaching away from the prior art, as many have identified garlic and onions as causing heartburn. Garlic (*allium sativum*), like onions, shallots and leeks, among others, belongs to the alliaceae family, and all contain organosulfur products. Garlic in particular contains allicin, an organosulfur compound that is produced when garlic is broken or crushed, through the action of the allinase enzyme on alliin. Allicin is a potent phytocide, with marked antibiotic and antifungal properties. The release of allicin produces other sulfur derivatives, such as ajoene, allyl sulfides, diallyl sulfides, allyl methyl disulfide, allyl methyl trisulfide, s-allyl cysteine and diallyl trisulfide. Allicin pronouncedly inhibits the secretion of various cytokines (IL-1b, IL-8, IP-10 and MIG) from epithelial cells, suppressing the expression of interleukin 8 (1-8) and interleukin 1b (IL-1b) mRN and is therefore considered to be effective in attenuating intestinal inflammation. It is believed that low doses of garlic oil suppress NOS (inducible Notric Oxide Synthase) activity, ulceration and apoptosis of the intestinal mucosa. At high doses, however, garlic oil has shown a toxic effect, which is why it is deduced that garlic is beneficial in moderate doses, but can be toxic in high doses. Garlic extracts and garlic oil have also been found to be powerfully anti-microbial against other GI bacteria such as *Escherichia coli, Shigella* sp, *Salmonella* sp, and *Proteus mirabilis*.

One aspect of the present invention is directed to the use of probiotics to modulate the human microbiota and promote health and prevent antibiotic side effects. L. species are acid-resistant and commensal and their concentrations in the normal human stomach vary between 0 and $10^3$ mL$^{-1}$. They can survive in the stomach for periods of up to 2 h. In various embodiments, fructo-oligosaccharides (FOS) and trans-galacto-oligosaccharides (TOS), such as inulin, are used to selectively stimulate growth and activity of health-promoting bacteria. In this regard, dietary inulin fibers are used to stimulate $Mg^{2+}$ and $Ca^{2+}$ absorption and are a potent stimulant of mineral absorption, especially achieved by oligofructose-enriched inulin. Certain strains of gut bacteria have a preference for inulin fibers. Thus, one aspect of the present invention is to selectively advance the population of such bacteria in a person's gut. It is known that N-butryic acid increases $Ca^{2+}$ and $Mg^{2+}$ absorption. Thus, certain embodiments of the present invention are directed to the provision of bacteria designed to produce n-butryic acid to treat PPI-induced $Ca^{2+}$ disturbances. It is believed that dietary inulin stimulates intestinal $Mg^{2+}$ absorption, and thus, other embodiments of the present method include the provision of dietary inulin in addition to the provision of the various bacteria strains as described herein. One aspect of the present invention is therefore directed to the impact of PPIs on $Ca^{2+}$ homeostasis and provides a treatment for PPI-induced mineral disturbances. Dietary oligofructose enriched inulin fibers are believed to prevent omeprazole-induced reduction of $Ca^{2+}$ absorption and lead to improved intestinal $Mg^{2+}$ absorption, thus preventing PPI-induced mineral deficits in individuals.

In various embodiments, the present invention is directed to the use of dietary inulin to counteract reduced intestinal $Ca^{2+}$ absorption upon PPI treatment. One aspect of the present invention is directed to the local luminal acidification of the colon to enhance intestinal $Mg^{2+}$ absorption and by so doing, preventing PPIH. Other embodiments are directed to the use of the fructan fiber inulin to reduce intestinal pH, such ingested inulin fibers being fermented in the large intestine by bifidogenic gut bacteria, resulting in short-chain fatty acids (SOFA), which in turn acidify the colon. Thus, one aspect of various embodiments is directed to the stimulating action of SOFA on intestinal $Mg^{2+}$ absorption by reducing the luminal pH. Certain aspects are directed to the enhancement of intestinal $Mg^{2+}$ and $Ca^{2+}$ absorption in order to counteract omeprazole-induced defects in mineral uptake. Proton-pump inhibitor-induced hypomagnesemia (PPIH) is the most recognized side effect of proton-pump inhibitors (PPIs). Additionally, PPIH is associated with hypocalcemia and hypokalemia. It is hypothesized that PPIs reduce epithelial proton secretion and thereby increase the pH in the colon, which may explain the reduced absorption of and $Mg^{2+}$ and $Ca^{2+}$. Fermentation of dietary oligofructose-enriched inulin fibers by the microflora leads to acidification of the intestinal lumen and by this enhances mineral uptake. One aspect of the present invention is therefore directed to the improvement of mineral absorption by application of dietary inulin to counteract PPIH.

As described in more detail herein, one aspect of the present invention involves the use of a natural small molecule derived from tomato plants, tomatidine, which is believed to cause cell growth, especially in skeletal muscle tissue. Tomatidine is an inhibitor of muscle atrophy and thus has a use as a therapeutic agent for skeletal muscle atrophy. Tomatidine is a steroidal alkaloid and the aglycone of alpha-tomatine, an abundant glycoalkaloid in tomato plants that mediates plant defense against fungi, bacteria, viruses and predatory insects. When consumed by animals, alpha-tomatine is hydrolyzed by stomach acid and intestinal bacteria to tomatidine, which is absorbed by the gut. Tomatidine is believed to have an anti-atrophic (anabolic) effect in skeletal muscle and possesses anti-hyperlipidemic and anti-atherosclerotic effects without evidence of toxicity. Tomatidine is significantly more potent than ursolic acid in building muscle tissue and has a different mechanism of action.

The tomato belongs to the Solanaceae family that includes more than 3,000 species. Tomato fruit consumption has been associated with a reduced risk of inflammatory processes, cancer, and chronic noncommunicable diseases (CNCD) including cardiovascular diseases (CVD) such as coronary heart disease, hypertension, diabetes, and obesity. Tomatidine is found in certain plants at certain developmental stages, such as in green (but not ripened red) tomatoes. One aspect of the present invention is directed to the provision to individuals in need thereof with bacteria that have been modified to produce effective amounts of tomatidine to address the muscle atrophy associated with various cancers. In one embodiment, DNA encoding tomatidine or its analogs is inserted into the genome of one or more bacterial species by employing CRISPR-Cas or CPf1 systems, such that an individual can orally take a pill containing such modified bacteria (preferably bacteria of the same species as presently reside in the individual's gut microbiome) and in such a manner, administer tomatidine to the individual in a manner that does not require injections or the taking of traditional pharmaceutical formulations containing tomatidine. In such a manner, the production by such bacteria inside the individual provides a more natural way for tomatidine to be provided to those in need of its extraordinary abilities to foster the retention of muscle mass in the individual. The ability to further modify the populations of bacteria inside an individual via the use of particular antibiotics, for example, those that can target the modified species that produce tomatidine, provides a way to control the amount of tomatidine in the individual's body. Tomatidine in this instance, is but one of many examples of how the personal microbiome of an individual can be amended, modified, enhanced and/or changed to adjust the levels and amounts of various compounds, drugs, molecules, etc. that are important in maintaining or restoring health to an individual.

Yet further embodiments include the increase in the levels of *Roseburia* in the gut of the individual human being. Other embodiments similarly involve increasing the levels of *Faecalibacterium prausnitzii* in the gut of the individual human being. Still others involve increasing the levels of bacterial species selected from the group consisting of *Bifidobacterium, Prevotella, Lachnospira*, and *Shigella*. It should be understood that in combating cancer, other embodiments involve administering to an individual human being bacteria that have been modified using a CRISPR-Cas system to produce p53. Such bacteria may be selected from the following in certain preferred embodiments: *Streptococcus, Actinomyces, Veillonella, Fusobacterium, Porphyromonas, Prevotella, Treponema, Neisseria Haemophilus, Lactobacillus, Capnocytophaga, Eikenella, Leptotrichia,*

*Peptostreptococcus, Propionibacterium, Chlamydia, Shigella flexneri, Mycoplasma bacteria, H. pylori*, and *Streptomyces hygroscopicus*.

Interventions using prebiotics require an initial presence of the bacterial group in order for it to grow. Bacteria including members of *Desulfovibrio*, Odoribacter, Oscillibacter, and Clostridioides genera prepares fecal microbiota transplant recipients via the secretion of metabolites, preferably coupled with administration of bacteria with bile-acid metabolizing activities, and leads to a restoration of health. Many of the preferred combinations of bacteria formulations as described herein include bacterial strains isolated from healthy humans, including bacteria that produce SCFAs, including butyrate-producing bacteria. In various embodiments of the present invention, a cocktail of different bacteria can be prepared to facilitate desired amounts and types of short chain fatty acids to be produced. Knowing which bacteria produce such SCFAs facilitates such combinations. The following bacteria produce acetate: *Akkermansia muciniphila, Bacteroides* spp., *Prevotella* spp. *Bifidobacterium* spp., *Clostridium* spp., *Ruminococcus* s pp., *Streptococcus* spp., *Blautia hydrogenotrophica, Coprococcus* spp. The following bacteria produce propionate: *Dialister* spp., Megasphaera elsdenii, *Bacteroides* spp., *Phascolarctobacterium succinatutens, Coprococcus catus, Veillonella, Roseburia inulinivorans, Ruminococcus obeum, Salmonella* spp. The following bacteria produce butyrate: *Coprococcus catus, Coprococcus comes, Anaerostipes* spp., *Coprococcus eutactus, Eubacterium hallii, Eubacterium rectal, Roseburia* spp., *Faecalibacterium prausnitzii, Clostridium butyricum, Ruminococcus, Anaerostipes* spp., *Coprococcus catus*. The gut microbiota supports the digestion and absorption of food, metabolizes fiber into bioactive short-chain fatty acids, produces vitamins and nutrients, maintains gut integrity, and modulates host immunity. SCFAs have beneficial effects on the intestinal barrier function and systemic anti-inflammatory effects, as well as roles in obesity, insulin resistance, and type 2 diabetes. SCFAs have been associated with response to immune checkpoint inhibitors (101) and have been shown to be the main metabolites produced by the gut microbiota of long-term responders to PD-1 antibody therapy.

In various embodiments of the present invention, bacteria are selected based upon their ability to produce bacteriocins. Bacteriocins are antimicrobial peptides that hamper growth of competing strains and are produced by specific strains of bacteria. In comparison to antibiotics, their mode of action rarely induces resistance.

With CRISPR systems, including but not limited to the CRISPR-Cas9 technology, formerly non-engineerable bacteria such as classical or next-generation probiotic strains or whole microbial communities can now be genetically modified. Many pathophysiological changes are induced not only by the bacteria involved, but also by the overproduction or lack of given metabolites. Examples include the short-chain acids acetate, butyrate, propionate, and lactate that are produced by the human microbiota and have important signaling functions in the human host. Various embodiments of the present invention are directed to microbiota-targeted interventions to ameliorate and reverse dysbiosis-associated pathophysiological changes.

Butyrate in particular has been shown, on the one hand, to enhance anti-tumour $CD8^+$ T-cell function through increasing IL-12 receptor and memory T-cell survival in vivo. Fecal butyrate has been associated with better anti-PD1 responses, but has also been noted to promote regulatory $CD4^+$ T cells and impair dendritic cell maturation, thus negatively associating with anti-CTLA4 efficacy. The importance of the role of the gut microbiome in responses is complex, extending beyond differential microbial abundances and encompassing complex interactions of the gut microbiome. The gut microbiome is unique in each individual and the gut mucosa is distinct from that found in stool. Thus, even within the same cancer (sub)type, there exists a uniqueness of the genetic and immune characteristics of each tumor. Having said this, however, it is possible to derive treatments based on the link between the human microbiome and immune checkpoint inhibitor responses, often foregoing the need for other combined toxic regimens of radiotherapy or chemotherapy. For example, oral glutamine supplementation can enhance the physical gut barrier and prevent or reduce disruption and increased permeability by normalizing intestinal permeability in patients with postinfectious diarrhea-predominant IBS. In addition, several embodiments of the present invention are directed to pre- and probiotics that are used to reinstate gut wall homeostasis. The non-digestible compounds in prebiotics are metabolized by gut microbiota and promote favorable gut microbiota composition and/or activity, resulting in beneficial physiological effects on the host. Suppletion with prebiotic inulin-type-6 fructans can reduce inflammation, promote mucosal healing, and induce functional and compositional microbiota changes.

The various combinations of bacterial compositions set forth herein provide a group of live microorganisms that can be beneficial to the host's health, promoting a favorable microbiota composition and functionality, improving physical gut barrier function, immunomodulation and modulating physiological processes on the host. Probiotic supplementation also enhances the therapeutic effects of immune checkpoint inhibitor therapy. For example, supplementation with a probiotic containing a butyrate producing bacterium such as *F. prausnitzii*, improves progression-free survival in patients with metastatic cancers.

Different gut microbiome compositions produce different biological effects because microbes are essentially chemical factories. A healthy microbiome reduces the likelihood of increased intestinal permeability (i.e. leaky gut), associated chronic inflammation and deficiency of short-chain fatty acids. Short-chain fatty acids (such as butyrate, which regulates intestinal permeability) are just one of the hundreds of postbiotic metabolites of microbial fiber fermentation in the gut. The gut microbiome also regulates and produces vitamins (K, B12 and folate), neurotransmitters (serotonin, dopamine, GABA, histamine and noradrenaline), amino acids and enzymes, all of which have direct and indirect effects on health and are strongly associated with mental wellbeing and cardiovascular disease, as well as obesity and autoimmune diseases. Nearly every disease involving inflammation is marked by a disordered microbiome profile that is deprived of key anti-inflammatory microbes (like *F. prauznizii*), and most modern diseases are associated with a lack of beneficial microbes feeding off plants and an abundance of disease-causing microbes.

"CRISPR" (Clustered Regularly Interspaced Short Palindromic Repeats) loci refers to certain genetic loci encoding components of DNA cleavage systems, for example, used by bacterial and archaeal cells to destroy foreign DNA. A CRISPR locus can consist of a CRISPR array, comprising short direct repeats (CRISPR repeats) separated by short variable DNA sequences (called spacers), which can be flanked by diverse Cas (CRISPR-associated) genes. The CR/SPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CR/SPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CR/SPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

As used herein, an "effector" or "effector protein" is a protein that encompasses an activity including recognizing, binding to, and/or cleaving or nicking a polynucleotide target. An effector, or effector protein, may also be an endonuclease. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes proteins encoded by a gene in a cas locus, and include adaptation molecules as well as interference molecules. An interference molecule of a bacterial adaptive immunity complex includes endonucleases. A Cas endonuclease described herein comprises one or more nuclease domains. A Cas endonuclease includes but is not limited to: the novel Cas-alpha protein disclosed herein, a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence.

CRISPR-Cas systems have been classified according to sequence and structural analysis of components. Multiple CRISPR/Cas systems have been described including Class 1 systems, with multi-subunit effector complexes (comprising type I, type III, and type IV), and Class 2 systems, with single protein effectors (comprising type II, type V, and type VI). A CRISPR-Cas system comprises, at a minimum, a CRISPR RNA (crRNA) molecule and at least one CRISPR-associated (Cas) protein to form crRNA ribonucleoprotein (crRNP) effector complexes. CRISPR-Cas loci comprise an array of identical repeats interspersed with DNA-targeting spacers that encode the crRNA components and an operon-like unit of cas genes encoding the Cas protein components. The resulting ribonucleoprotein complex recognizes a polynucleotide in a sequence-specific manner. The crRNA serves as a guide RNA for sequence specific binding of the effector (protein or complex) to double strand DNA sequences, by forming base pairs with the complementary DNA strand while displacing the noncomplementary strand to form a so-called R-loop. RNA transcripts of CRISPR loci (pre-crRNA) are cleaved specifically in the repeat sequences by CRISPR associated (Cas) endoribonucleases in type I and type III systems or by RNase III in type II systems. The number of CRISPR-associated genes at a given CRISPR locus can vary between species.

Different cas genes that encode proteins with different domains are present in different CRISPR systems. The cas operon comprises genes that encode for one or more effector endonucleases, as well as other Cas proteins. Some domains may serve more than one purpose, for example Cas9 comprises domains for endonuclease functionality as well as for target cleavage, among others. The Cas endonuclease is guided by a single CRISPR RNA (crRNA) through direct RNA-DNA base-pairing to recognize a DNA target site that is in close vicinity to a protospacer adjacent motif (PAM). Class I CRISPR-Cas systems comprise Types I, Ill, and IV. A characteristic feature of Class I systems is the presence of an effector endonuclease complex instead of a single protein. A Cascade complex comprises a RNA recognition motif (RRM) and a nucleic acid-binding domain that is the core fold of the diverse RAMP (Repeat-Associated Mysterious Proteins) protein superfamily.

Type I CRISPR-Cas systems comprise a complex of effector proteins, termed Cascade (CRISPR-associated complex for antiviral defense) comprising at a minimum Cas5 and Cas7. The effector complex functions together with a single CRISPR RNA (crRNA) and Cas3 to defend against invading viral DNA. Type I systems are divided into seven subtypes.

Type III CRISPR-Cas systems, comprising a plurality of cas7 genes, target either ssRNA or ssDNA, and function as either an RNase as well as a target RNA-activated DNA nuclease. Type IV systems, although comprising typical type I cas5 and cas7 domains in addition to a cas8-like domain, may lack the CRISPR array that is characteristic of most other CRISPR-Cas systems.

Class II CRISPR-Cas systems comprise Types II, V, and VI. A characteristic feature of Class II systems is the presence of a single Cas effector protein instead of an effector complex. Types II and V Cas proteins comprise an RuvC endonuclease domain that adopts the RNase H fold. Type II CRISPR/Cas systems employ a crRNA and tracrRNA (trans-activating CRISPR RNA) to guide the Cas endonuclease to its DNA target. The crRNA comprises a spacer region complementary to one strand of the double strand DNA target and a region that base pairs with the tracrRNA (trans-activating CRISPR RNA) forming a RNA duplex that directs the Cas endonuclease to cleave the DNA target, leaving a blunt end. Spacers are acquired through a not fully understood process involving Cast and Cas2 proteins. Type II CRISPR/Cas loci typically comprise cast and cas2 genes in addition to the cas9 gene. Type II CRISR-Cas loci can encode a tracrRNA, which is partially complementary to the repeats within the respective CRISPR array, and can comprise other proteins such as Csn1 and Csn2. The presence of cas9 in the vicinity of cast and cas2 genes is the hallmark of type II loci. Type V CRISPR/Cas systems comprise a single Cas endonuclease, including Cpf1 (Cas12) that is an active RNA-guided endonuclease that does not necessarily require the additional trans-activating CRISPR (tracr) RNA for target cleavage, unlike Cas9. Type VI CRISPR-Cas systems comprise a cas13 gene that encodes a nuclease with two HEPN (Higher Eukaryotes and Prokaryotes Nucleotide-binding) domains but no HNH or RuvC domains, and are not dependent upon tracrRNA activity. The majority of HEPN domains comprise conserved motifs that constitute a metal-independent endoRNase active site. Because of this feature, it is thought that type VI systems act on RNA targets instead of the DNA targets that are common to other CRISPR-Cas systems. To comply with written description and enablement requirements, incorporated herein by the following references are the following patent publications: 2014/0349405 to Sontheimer; 2014/0377278 to Elinav; 2014/0068797 to Doudna; 20200190494 to Hou, et. al.; and 2020/0199555 to Zhang; U.S. Pat. No. 9,585,920 to Kovarik; US Pat. Publication No. 20170106026 to Kovarik, and U.S. Pat. No. 9,457,077 to Kovarik; US Pat. Publication No. 20170021011 to Kovarik; US Pat. Publication No. 20170173085 to Kovarik.

In certain embodiments, it may be advantageous to genetically modify a gut mucosal-associated bacteria with polynucleotides and as taught herein to express or overexpress the polynucleotides as taught herein or to produce or overproduce the polypeptides, such as butyrate and acetate, directly into the vicinity of, or within the gut mucosal barrier of a human. In a preferred embodiment, the gut mucosal-associated bacteria may be any bacteria from the species *F. prausnitzii, Prevotella intermedia,* and/or *Akkermansia muciniphilla*. Such overproduction may be realized by genetic modification tools involving recombinant DNA technologies, genome editing such as by using tools based on CRISPR/cas-like systems, or by classical mutation selection systems.

In an embodiment, the genetically modified host cell may be any bacteria, particularly one which is not from a species of bacteria that naturally occurs or lives in the vicinity of or within the gut mucosal barrier of a mammal. Non-limiting examples of such bacteria include any beneficial isolated intestinal bacterial strains, e.g. probiotic bacteria, particularly strains selected from the genera *Lactococcus, Lactobacillus,* or *Bifidobacterium* may be used. In addition, strict anaerobic intestinal bacteria may be used such as those belonging to the genera known to occur in the human intestinal tract. As described herein, in various embodiments, strictly anaerobic bacteria are encapsulated or microencapsulated to avoid contact with oxygen, and are delivered to a human such that the encapsulation is dissolved or fractured to release such bacteria in a portion of the body, e.g. gut, where it can thrive.

Certain embodiments are directed to the targeted manipulation of the gut microbiome for therapeutic applications, such as the manipulation of the gut microbiome achieved by altering the microbiota population and composition, or by modifying the functional metabolic activity of the microbiome to promote health and restore the microbiome balance. There has been recent progress in the engineering of gut commensals, which also presents great potential for biomedical applications. Specifically, in *Bacteroides* thetaiotaomicron, components for tunable gene expression were developed and characterized and expected functional outputs were observed in mice after administration of these engineered *B. thetaiotaomicron*. Thus, one aspect of various embodiments is to harness such engineered commensals, especially *F. prausnitzii* for the overproduction of butyrate, for therapeutic purposes.

*F. prausnitzii* was first isolated in 1922 by C. Prausnitz. Morphologically, *F. prausnitzii* is a Gram-negative, non-motile and non-sporeforming rod with a diameter of 0.5 to 0.9.times.2.4 to 14.0.mu.m. *F. prausnitzii* is a strictly anaerobic bacterium that produces butyrate, formate, D-lactate and $CO_2$ but no hydrogen as fermentation products and *F. prausnitzii* growth is inhibited by acidic pH and bile salts. The amount of *F. prausnitzii* in the healthy human gut is linked to diet. Inulin-derived prebiotics have been shown to significantly increase *F. prausnitzii* concentration in the gut. *F. prausnitzii* is statistically linked to eight urinary metabolites: dimethylamine, taurine, lactate, glycine, 2-hydroxyisobutyrate, glycolate, 3,5-hydroxylbenzoate and 3-aminoisobutyrate. It is believed that *F. prausnitzii* has pronounced anti-inflammatory effects. While not bound by theory, *F. prausnitzii* may induce an increased secretion of an anti-inflammatory cytokine interleukin 10, and a decreased secretion of pro-inflammatory cytokines like interleukin 12 and tumor necrosis factor—a production. It is further believed that *F. prausnitzii* has the ability to suppress inflammation, and it is hypothesized that this is due to metabolite(s) secreted by *F. prausintzii*, including but not limited to butyrate. The number of *F. prausnitzii* is significantly higher in the gut of healthy subjects as compared to IBD and it is believed that *F. prausnitzii* is crucial to gut homeostasis and disease protection. *F. prausnitzii* is one of the most abundant bacteria in a healthy human gut and is believed to have a positive effect on the human gut health. *F. prausnitzii* belongs to the *Clostridium leptum* group (*Clostridium* cluster IV), belonging to phylum Firmicutes (Lineage: Bacteria; Firmicutes; Clostridia; Clostridiales; Ruminococcaceae; *Faecalibacterium; Faecalibacterium prausnitzii*). *F. prausnitzii* has been previously called *Fusobacterium prausnitzii* (also cited as *F. prausnitzii*), with it only distantly being related to Fusobacteria and more closely related to members of *Clostridium* cluster IV.

Moderate butyrate levels can prevent high-fat-diet-induced insulin insensitivity through epigenetic regulation, and mitochondrial beta-oxidation. *F. prausnitzii* is one of the unique organisms that reduce various autoimmune diseases, especially type-1 diabetes via the modulation of gut epithelium homeostasis and immune system. Studies associated with gut microbiota and type-1 diabetes have a lower proportion of butyrate-producing organisms, such as Firmicutes and *Clostridium*, which protects against autoimmune diabetes. While not bound by theory, *F. prausnitzii* is believed to regulate the development of autoimmune diabetes via butyrate dependent complementary pathways. An abundant quantity of butyrate can lower the gut barrier function and enhance cell apoptosis, with high levels of butyrate stimulating GLP-1 secretion and enhancing insulin sensitivity through cAMP signals, such as PKA and Epac, which inhibit gastric emptying. Due to the inhibition of gastric emptying, butyrate can be excreted slowly and accumulates, influencing the anti-inflammatory potential, pH, and oxidative stress.

Butyrate is the major product of carbohydrate fermentation in the colon. Butyrate modulates several processes and is a known anti-proliferative agent. In cultured cell lines, butyrate inhibits DNA synthesis and cell growth, mainly by inhibiting histone deacetylase. Butyrate is also suggested to regulate the citric acid cycle, fatty acid oxidation, electron transport and TNF-.alpha. signaling. Animal studies have indicated that butyric acid may have antineoplastic properties, which means that it may protect against colon cancer. As dietary fiber is protective against colon cancer because carbohydrates entering the large bowel stimulate the production of butyrate. Butyrate has also been suggested to provide protection against ulcerative. *F. prausnitzii* is an important producer of butyrate, and the decrease of *F. prausnitzii* has been correlated to lower concentrations of fecal butyrate in healthy human subjects and it is believed that *F. prausnitzii* plays an important role in the protection of the colon. While not bound by theory, the benefits of butyrate are thought to depend on several aspects, such as time of exposure and butyrate amount. Increased butyrate production by *F. prausnitzii* is therefore a desired outcome and employment of CRISPR systems to achieve the same, employing the known genes involved in butyrate by *F. prausnitzii* is one important embodiment of the present invention.

Studies have shown that there was a statistically significant reduction in the *F. prausnitzii* abundance during both fiber-free and fiber-supplemented diets, but it is postulated that the reduction during the fiber-supplemented diet was due to the use of pea fiber, which is not believed to support the growth of *F. prausnitzii*, and thus, with the proper fiber being employed, the increase in butyrate production is achieved. In situations where there is insufficient fiber for the beneficial bacteria to consume, the bacteria end up eroding the mucus of the gut and leads to epithelial access by mucosal pathogens.

The relative abundance of Bacteroidetes and Firmicutes has been linked to obesity, with the Firmicutes ratio being significantly higher in obese individuals. It is believed that a high number of *F. prausnitzii* leads to higher energy intake, because *F. prausnitzii* is responsible for a significant proportion of fermentation of unabsorbed carbohydrates in the gut.

*F. prausnitzii* cultivation has proven difficult because the bacterium is a strictly obligatory anaerobe that does not tolerate any oxygen. As described herein, encapsulation of *F. prausnitzii* is achieved such that it can be effectively delivered such that the encapsulated structure can degrade or be fractured at an appropriate time and place to release such bacteria to a human to derive beneficial results, e.g. the increased production of butyrate. For example, microencapsulation, in a xanthan and gellan gum matrix, and a subsequent freeze-drying protocol can be employed to achieve this result.

In other embodiments, the bacterial composition employed includes both *F. prausnitzii* and *Akkermansia muciniphila*, another abundant member of the human gut microbiota. It is further believed that *Faecalibacterium prausnitzii* plays a vital role in diabetes and can be used as an intervention strategy to treat dysbiosis of the gut's microbial community that is linked to the inflammation, which precedes autoimmune disease and diabetes.

The microbiota in adults is relatively stable until the persons get 60 years old. Gut alterations lead to elevated gut permeability and reduced gut mucosal immunity, contributing to the development of various cancers, autoimmune disorders, inflammatory bowel diseases, metabolic syndrome and neurodegenerative diseases. The resultant elevated intestinal permeability is a consequence of reduced expression of tight junction proteins that favors the uncontrolled passage of antigens and enables the translocation of bacterial lipopolysaccharide to the gut connective tissues and to the blood circulation, causing insulin resistance and metabolic endotoxemia.

The gastrointestinal tract pH normally ranges between 5 and 5.5 in the ileum and the colon has a range from 6.6 to 7.0, which is one of the main factors in constructing the shape of the microbial communities in the colon. Diet compositions containing fermentable polysaccharides are regulators of the intestinal pH, which facilitates a more acidic environment through the end-products of SCFAs in the gut.

An individual generally represents a unique collection of genera and sub-species and it may be different based on the diet (vegetarian or Western with high protein or fat), the age of the host organism, genetic and environmental factors. Diet greatly influences the diversity of the microbiota in the gut and the microbiota is genetically well equipped to utilize various nutritional substrates to maintain a normal gut microbiota pattern. An adequate SOFA (butyrate) production level is essential for gut integrity and butyrate-producing bacteria, such as *Eubacterium, Fusobacterium, Anaerostipes, Roseburia*, Subdoligranulum, and *Faecalibacterium*, but especially, *F. prausnitzii*, have the potential of anti-inflammatory effect and help to reduce bacterial translocation, improve the organization of tight junctions and stimulate the secretion of mucin to maintain the integrity of the gut, with beneficial effects against inflammation in the gut.

Inflammation is one of the major pathophysiological factors leading to insulin resistance and progressively causes type-2 diabetes. *F. prausnitzii* counts significantly decreased in diabetic individuals with negative correlation to glycated hemoglobin HbA1c values. Along with *Akkermansia muciniphila, F. prausnitzii* is abundantly found in individuals with normal glucose tolerance compared to the pre-diabetic subjects. *F. prausnitzii* can convert acetate into butyrate using butyryl-CoA:Acetate CoA-transferase (BUT) pathways, thereby providing a balanced pH in the gut.

Throughout evolution, bacteria progressively acquired virulence factors and the disease-promoting and pro-carcinogenic effects of pathogens depend on these virulence factors, which often comprise adhesion molecules, which confer the ability to adhere to and invade the tissues of the human body. One aspect of the present invention is directed to the modification of such adhesion molecules so that pathogenic bacteria are altered in a manner that reduces their abilities to adhere to tissues of the human body, thus lessening various human diseases.

Chronic and/or excessive consumption of alcohol has been found to be an important risk factor for many cancers, including colorectal cancer. Microbial metabolism may contribute to the toxicity of alcohol, especially in the gastrointestinal tract, where aerobic and facultative anaerobic bacteria convert ethanol to acetaldehyde. Indeed, acetaldehyde is known to be a highly toxic and pro-carcinogenic compound with various negative effects, ranging from DNA damage and impaired DNA excision repair to the degradation of folate. Thus, one aspect of various embodiments of the present invention is directed to providing particular bacteria to a person who consumes alcohol in a manner that lessens the risk of cancer via the ability of such bacteria to ameliorate the accumulation of acetaldehyde. The conversion of ethanol to acetaldehyde is inhibited by the use of antibiotics, such as ciprofloxacin, which kills primarily aerobic and facultative anaerobic bacterial populations. Thus, to reduce the undesired effects of alcohol conversion to acetaldehyde, the use of specific antibiotics, followed by the use of probiotics and/or fecal transplantation protocols, is one aspect of the present invention that may be employed to combat colorectal cancer-associated dysbiosis and thus restore eubiosis in chronic diseases, helping to reduce microbiota-induced genotoxicity and activation of inflammatory, proliferative and pro-carcinogenic pathways. The gut microbiota plays a major role in the promotion and progression of colorectal cancer via several mechanisms, including inflammation, metabolism, and genotoxicity, and thus, targeting an individual's microbiota is an effective way to treat, if not prevent, colorectal cancer. Particular bacterial species have been identified that are suspected to play a role in colorectal carcinogenesis, including *Streptococcus bovis, Helicobacter pylori, Bacteroides fragilis, Enterococcus faecalis, Clostridium septicum, Fusobacterium* spp. and *Escherichia coli*. Cancer incidence is low in the Ohio Amish and it is believed by the present inventors that the presence of *Prevotella* bacteria as more predominant bacteria in both their oral and gut microbiomes, is related to such lower cancer incidence. The gut microbiota of various livestock species has been reported to contain a high relative abundance of the xylanolytic bacterial species *Prevotella*. The present inventors submit that the environment plays an important role in modulating bacterial community composition and that transmission of gut microbes occurs across host species. Gut microbial communities often contain many

*Bacteroides* or their close relatives, *Prevotella*. One aspect of certain embodiments of the present invention is directed to increasing the prevalence of *Prevotella* populations in individuals so as to lessen the chances of cancer developing in such individuals. Still other embodiments are directed to the modification of *Prevotella* bacteria in a manner that makes them less virulent, but that still maintain the beneficial effects of such bacteria in various microbiomes, such as the oral and gut microbiomes, e.g. by reducing the expression of virulence factors of *Prevotella*.

The composition of gut microbiota evolves throughout human life, from birth to old age, and is modulated, temporarily or permanently, by many factors such as dietary components, environment, age, stress, treatment (medical or surgical) and disease. Antibiotic-based therapy represents one of the most important factors with the effect on the composition of the microbiota. This therapy can cause diarrhea which generally is associated with altered intestinal microbiota resulting in enteropathogens overgrowth, loss of mucosal integrity and altered metabolism of vitamins and minerals. The elderly have significantly different microbiota than younger adults.

Individuals can be classified into one of three prevalent variants or "enterotypes" according to the abundance of predominant genera which are *Bacteroides*, *Prevotella* and *Ruminococcus*. *Bacteroides* enterotypes are related to amino acids, animal proteins and saturated fats, constituents typical to Western diet, while *Prevotella* is connected to carbohydrates and simple sugars, suggesting an interconnection with a carbohydrate-based diet more common of rural societies.

Individuals whose microbiota are mainly *Bacteroides* and commute their dietary patterns to a diet based on high proportions of carbohydrates, will acquire a *Prevotella* enterotype in the long term. Substantial changes in the composition of fecal microbiota are detectable in a few days after carbohydrate intake, demonstrating that diet rapidly and reproducibly alters the human gut microbiome. Numerous studies indicate that fruit, vegetable and a high-fiber intake, particularly of cereals and whole grains, is associated with a decreased risk of colorectal cancer, while diets that are rich in red and processed meat, fat and alcohol are associated with an increased risk of the disease. Higher dietary intakes of animal products may modify gut microbiota and consequently play an important role in carcinogenesis.

In various embodiments, re-cultivated human intestinal microbiota obtained by cultivation of a stool sample in a cultivation medium is employed to promote the proliferation of select bacteria, including at least two of the following Phyla: Bacterioidetes, Firmicutes, Proteobacteria and Actinobacteria, and more preferrably at least two of the following: *Faecalibacterium*, *Lachnospira*, *Veillonella*, *Rothia*; *Lactobacillus johnsonii* and *Prevotella*. In other embodiments, one or more of the following microorganisms is employed: *Bifidobacterium lognum*, *B. infantis* BCRC 14602; *Prevotella; Ruminococcus, Bifidobacterium infantis, Lactobacillus acidophilus, Bacteroides fragilis, B. longum* bv. *infantis* isolate UCD272; *B. infantis* BCRC; *B. longum* bv. *infantis*, AY151398; and *Lactobacillus ruminus; L. lactis, L. lactis cremoris, L. plantaru*, and *L. raffinolactis; Faecalibacterium, Lachnospira, Veillonella*, and *Rothia; Lactobacillus johnsonii, Lactobacillus crispatus, Lactobacillus brevis, Lactobacillus buchneri, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus rhamnosus, Lactobacillus salivarius, Streptococcus thermophilus, Lactococcus lactis, Lactococcus plantarum, Lactococcus raffinolactis, Leuconostoc lactis, Leuconostoc mesenteroides, Enterococcus faecalis*, and *Enterococcus faecium; Enterococcus faecalis; Lactobacillus reuteri*, and *Lactobacillus paracasei*. In certain embodiments, the method includes the use of a mixed culture of bacterial cells of three to eight species of lactic acid bacteria. In particular mixed cultures, the following may be included: *Saccharomyces cerevisiae, Lactobacillus delbrueckii, Lactobacillus acidophilus, Lactobacillus plantarum, Lactobacillus fermentum, Lactobacillus casei, Lactobacillus rhamnosus, Lactococcus lactis* and *Streptococcus thermophilus; Enterococcus faecium; Bacillus coagulans; Leuconostoc, Pediococcus, Lactobacillus casei, Lactobacillus plantarum, Lactococcus lactis* subspecies *lactis, Lactococcus lactis* subspecies *cremoris; Lactobacillus plantarum; Pediococcus pentosaceus; Streptococcus thermophilus; Lactobacillus paracasei; Lactobacillus plantarum, Lactobacillus gasseri* and *Lactobacillus salivarius; Lactobacillus acidophilus* PM-A0002, *Lactobacillus gasseri, Lactobacillus salivarius, Lactobacillus acidophilus* PM-A0013; *Leuconostoc mesenteroides; Lactobacillus bulgaricus, Lactobacillus rhamnosus, Lactobacillus acidophilus, Lactobacillus paracasei; Bifidobacterium bifidum; Lactobacillus brevis; Enterococcus durans; Leuconostoc mesenteroides; Lactobacillus* crispatus. Still other embodiments of the invention may comprise extracts obtained from one or more of the following species: *Lactobacillus fermentum, Lactobacillus rhamnosus, Lactobacillus plantarum, Lactobacillus johnsonii, Lactobacillus helveticus, Lactobacillus casei* defensis, *Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius*, and *Lactobacillus lactis*. In some embodiments, at least one strain from each of the above species of bacteria is used, while in other embodiments, one or more specific strains from the list above may be removed or substituted with one or more different strains. In particular, some embodiments of the present invention comprise an extract obtained from one or more of the following bacterial strains: *Lactobacillus fermentum* 1-3929, *Lactobacillus rhamnosus* 71.38, *Lactobacillus plantarum* 71.39, *Lactobacillus johnsonii* 103782, and *Lactobacillus helveticus* 103146; *Lactobacillus fermentum* 1-3929, *Lactobacillus rhamnosus* 71.38, *Lactobacillus plantarum* 71.39, *Lactobacillus johnsonii* 103782, and *Lactobacillus helveticus* 103146. The following bacteria species may also be employed: *Lactobacillus acidophilus* PM-A0002 deposit number M 207038, *Lactobacillus* gasseri PM-A0005 deposit number M 207039, *Lactobacillus salivarius* PM-A0006 deposit number M 207040, *Lactobacillus johnsonii* PM-A0009 deposit number M 207041 and *Lactobacillus acidophilus* PM-A0013 deposit number M207042. Certain other embodiments of the present invention include a combination of particular bacterial strains, selected from the group consisting of *Prevotella; Lactobacillus johnsonii; Bacteroides fragilis, Lactobacillus ruminus*, and at least one of *B. longum* bv. *infantis* isolate UCD272 or *B. longum* bv. *infantis*, AY151398. In more preferred embodiments, the gut microbiome of an individual is modified by providing in preferably a pill form a collection of microbes that include at least two of the following Phyla: Bacterioidetes, Firmicutes, Proteobacteria and Actinobacteria, and more preferrably at least two of the following: *Faecalibacterium, Lachnospira, Veillonella, Rothia; Lactobacillus johnsonii* and *Prevotella*.

As one of ordinary skill in the art will appreciate, one must give value to their existence by behaving as if one's very existence were a work of art. You must have chaos within you to give birth to a dancing star. And those who were seen dancing were thought to be insane by those who could not hear the music. To live is to suffer, to survive is to find some meaning in the suffering. No one can construct for you the bridge upon which precisely you must cross the stream of life, no one but you yourself alone. There will always be rocks in the road ahead of us. They will be stumbling blocks or stepping stones; it all depends on how you use them. The center is everywhere. Bent is the path of eternity.

In still other embodiments, interspecies interactions within mixed microbial communities is involved, with the objective being to modify competitive relationships involving nonbiocidal biosurfactants, enzymes, and metabolites produced by bacteria and other microorganisms in a manner such that selection of particular bacterial species can be employed to do one or more of inhibit initial adhesion, trigger matrix degradation, encourage jamming of cell-cell communications, and induce biofilm dispersion. Nonbiocidal molecules are thus employed to modify competitive interactions within biofilms in a manner that promotes the overall health of an individual's microbiome.

The foregoing has outlined rather broadly various pertinent and important features of various embodiments of the present invention. Such description is, however, not to be considered as limiting the invention in any way. The invention is capable of other embodiments and of being practiced and carried out in various ways which will become obvious to those skilled in the art who read this specification. Also, it is to be understood that the phraseology and terminology employed herein are for the purpose of description and should not be regarded as limiting of the invention in any fashion.

*F. prausnitzii* is a multi-skilled commensal organism and a chief member of human microbiota. It is broadly distributed in the digestive tract of mammals and also in some insects. It is rich in the hind gut rather than in the stomach, as well as jejunum. The consumption of a higher quantity of animal meat, animal fat, sugar, processed foods, and low fiber diet (the typical westernized diet) reduces the count of *F. prausnitzii*, while a high-fiber (vegetables and fruits) and low meat diet enhance the count of *F. prausnitzii*. It is known to consume a variety of diet containing polysaccharides, such as the prebiotic inulin, arabinoxylans, apple pectin, oligofructose, resistant starch, fructan supplement, pectins and some host-derived carbon sources (including d-glucosamine and N-Acetyl-d-glucosamine). Meta-analyses also show that the increased consumption of fiber significantly reduces the risk of mortality.

Certain embodiments of the present invention relate to using a *Roseburia* sp. strain, and preferably *Roseburia intestinalis*, to reduce the likelihood of and to treat fatty liver disease, whether that be NALFD, ALD or NASH. Using *Roseburia* sp. the following benefits may be achieved: tight junctions between epithelial cells are strengthened and epithelial resistance of epithelial cell membranes is increased; the concentration of blood lipopolysaccharide (LPS) is reduced; and there is a reduction in liver damage and a reduction of triglycerides of liver. A composition containing the *Roseburia* sp. strain of the present invention may be administered orally, parenterally, or sublingually, as a tablet form containing starch or lactose, or a capsule form alone or containing an excipient. A preferred dose of a composition containing the *Roseburia* sp. may differ according to the age, body weight, gender, administration form, health condition, and disease degree of patients, but in one preferred embodiment, a daily dose is at least 550 mg/kg. Certain embodiments include a food or beverage that includes *Roseburia* sp. to reduce the likelihood of NAFLD or NASH. While a PHOSITA will appreciate that *Roseburia* sp. strains may be employed to treat NAFLD and NASH, other aspects of the present invention can be used to detect an individual with NALFD or NASH via low counts of *Roseburia* sp. Increasing the levels of *Roseburia* sp. in an individual is believed to treat such individual with respect to NAFLD and NASH.

One will appreciate that this Summary of the Invention is not intended to be all encompassing one of skill in the art will appreciate that the entire disclosure, as well as the incorporated references, provides a basis for the scope of the present invention as it may be claimed now and in future applications.

BRIEF DESCRIPTION OF THE DRAWINGS

FIG. 1 is an illustration depicting the visual difference in appearance between a normal liver and a liver with non-alcoholic fatty liver disease.

DETAILED DESCRIPTION OF PREFERRED EMBODIMENTS

Probiotic therapies can reduce liver aminotransferases, total-cholesterol, TNF-α and improve insulin resistance in NAFLD patients. Modulation of the gut microbiota represents a new treatment for NAFLD. In certain embodiments, the methods and systems as described herein are directed to inhibiting glucosphingolipid synthesis in an individual by provision of particular microbes effective to achieve such inhibition. In other embodiments, an engineered autonomously distributed circuit that contains a programmable nuclease able to target a virulence factor or an antibiotic resistance gene of the bacterial species is employed, whether they be Gram-negative bacterial cells, Gram-positive bacterial cells, or a combination thereof. Microbial cells may include members of the phyla Actinobacteria, Bacteroidetes, Proteobacteria, Firmicutes, or a combination thereof. In particular embodiments, gut bacteria are modified to address the synthesis of triacylglycerol. There is a direct correlation between high triacylglycerol (triglyceride; TAG) levels and the severity of metabolic syndrome. Thus, controlling the synthesis of TAG will have a great impact on overall systemic lipid metabolism and thus metabolic syndrome progression.

The Acyl-CoA: monoacylglycerolacyltransferase (MGAT) family has three members (MGAT1, -2, and -3) that catalyze the first step in TAG production, conversion of monoacylglycerol (MAG) to diacylglycerol (DAG). TAG is then directly synthesized from DAG by a Acyl-CoA: diacylglycerolacyltransferase (DGAT). The conversion of MAG.fwdarw.DAG.fwdarw.TAG is the major pathway for the production of TAG in the small intestine, and produces TAG to a lesser extent in the liver.

One aspect of various embodiments of the present invention is directed towards the therapeutic potential of inhibiting MGAT for lowering TAG synthesis. Elevated plasma TAG has been associated with an increased risk of coronary and cerebrovascular ischemic events. Excessive TAG synthesis in the intestine due to dietary fat absorption followed by increased accumulation of TAG in the liver and adipose plays an integral role in the progression of metabolic disorders including obesity, insulin resistance, T2D, and fatty liver disease. Limiting TAG production in humans provides a way to address these metabolic disorders.

TAG is de novo synthesized in the liver and adipose tissue, while dietary TAG is broken down and re-synthesized in the small intestine. In the liver, TAG is used for very low density lipoprotein (VLDL) assembly. Newly formed VLDL is secreted into the circulatory system where it transports neutral lipids including TAG to peripheral tissues. In the small intestine, dietary TAG is hydrolyzed by pancreatic lipase to FA and MAG that are re-absorbed in the intestinal lumen. Enterocytes then re-synthesize TAG and secrete it as ApoB-containing chylomicrons that deliver dietary fat to tissues. Most tissues including liver and adipose use the G3P pathway for the synthesis of TAG. In contrast, the small intestine predominately relies on the MAG pathway.

MGAT is a major regulator of TAG homeostasis in response to diet. In humans, the expression of MGATs is up-regulated in the livers of insulin-resistant patients who have nonalcoholic fatty liver disease (NAFLD). MGAT has related acyltransferases (DGAT) and they share similar molecular relationships, however, MGAT genes share homology with DGAT2 and not DGAT1. DGAT1 is mainly expressed in adipose and small intestine tissues; DGAT2 is expressed in liver tissue. There exists a fundamental role for DGAT2 in TAG biosynthesis, much more so than DGAT1.

There presently are very few therapeutics existing to treat NAFLD. Various aspects of the present invention relate to the inhibition of MGAT2 to lower TAGs and to also reduce or eliminate the progression of NAFLD, which ultimately progresses to NASH, and later cirrhosis. In certain embodiments, protection of the liver from developing NASH involves the inhibition of MGAT2 synthesis (rather than MGMAT1). Thus, various embodiments of the present invention are directed to the protection of the liver from developing NASH by effective inhibition of MGAT2 synthesis by employing bacteria of an individual's microbiome, especially using bacteria modified via CRISPR-Cas systems to achieve inhibition of MGAT2 synthesis.

In still other embodiments, protection of the liver from developing NASH involves the inhibition of MGAT3 synthesis. The MGAT3 gene, Mogat3, exists only in higher mammals and not in rodents. Thus, employment of bacterial systems, especially engineered gut microbes that carry inhibitors of Mogat3, is one method and system to achieve the treatment, likelihood of prevention and the prevention of NAFLD. The sequence of MGAT3 is more homologous to DGAT2 than to MGAT1 or MGAT2. Thus, MGAT3 exhibits significantly higher DGAT activity than MGAT1 and MGAT2. MGAT3 expression levels increase in patients with NAFLD and its levels decrease after gastric bypass surgery-induced weight loss. It is therefore believed that MGAT3 plays a more important role than MGAT2 in obesity related hepatic insulin resistance and NAFLD progression in humans. In various embodiments of the present invention either the expression of MGAT2 or MGAT3, or both, is employed to combat NAFLD, and in particular, via the employment of modified gut bacteria via enhancement of such expression by use of the CRISPR-Cas/Cpf1 systems as described herein.

While the inhibition of human intestinal DGAT enzyme blocks TAG synthesis completely and has led to severe fat malabsorption, the use of DGAT1 inhibitors as anti-diabetes and/or anti-obesity agents is not favored due to gastrointestinal side effects. One aspect of the present invention is directed to achieving the reduction of TAG synthesis without these gastrointestinal side effects.

In human liver tissue, MGAT2/MGAT3 expression is correlated with the progression of NAFLD. In the small intestine, MGAT2 inhibition results in changes in TAG absorption and synthesis, as well as incretin secretion. These actions contribute to weight loss, improvement of insulin sensitivity and hypertriglyceridemia, and the prevention of NAFLD progression. While the blocking of dietary TAG absorption using inhibitors to DGAT1 exhibit unwanted gastrointestinal side effects, the targeting of the MAG pathway as a therapeutic for metabolic syndrome is a viable option for inhibiting intestinal TAG synthesis without such side effects. Inhibition of intestinal MGAT2 results in dynamic changes in TAG and cholesterol absorption, which leads to the changes in systemic energy balance and gut incretin release. Inhibition of the MGAT2 isozyme in the liver improves steatosis by attenuating fat accumulation and insulin resistance. In adipose, MGAT2 inhibition reduces fat biosynthesis and improves glucose uptake. Thus, one aspect of the present invention relates to either or both MGAT3 and MGAT2 inactivation in various tissues, especially by employing modified gut bacteria as described herein, to achieve the benefits of reducing body weight, improving insulin resistance, decreasing hyperlipidemia, and attenuating hepatic steatosis.

Acyl-CaA:diacylglycerol acyltransferase (DGAT) catalyzes the final step in triglyceride synthesis by facilitating the linkage of sn-1,2 diacylglygerol (DAG) with a long chain acyl CoA. There are two primary isoforms of DGAT, DGAT-1 and DGAT-2. DGAT-1 is primarily expressed in the small intestine while DGAT-2 exhibits primarily hepatic expression where its expression is insulin responsive. Inhibiting expression of DGAT-2 significantly improves hepatic steatosis. Thus, the materials and methods of various embodiments of the present invention can be used to alter expression of DGAT-2 for the treatment of NASH and NALFD, and to reduce hepatic insulin resistance. While certain aspects of the present invention can involve the use of engineered nucleases to knock out DGAT-2 in a subset of liver cells, or involve the use of an engineered transcription factor that can be used to down-regulate DGAT-2 expression, other more preferred treatment methods employ the use of CRISPR-Cas or Cpf1 systems to inhibit DGAT-2 expression.

In still other embodiments, the present invention is directed to addressing primary sclerosing cholangitis (PSC), a disease that involves severe inflammation and scarring that develops in the bile ducts and is associated with patients who suffer from IBD. Those with PSC may ultimately require liver transplantation. The cause is not known and there is no effective medication for PSC. Primary biliary cirrhosis is a chronic inflammatory intrahepatic liver disorder that slowly destroys the small-to-medium-sized bile ducts within the liver. When these ducts are damaged, bile builds up in the liver (cholestasis) and over time damages liver tissue. Primary sclerosing cholangitis is a similar, but affects the part of the bile duct that is outside of the liver. In both diseases, inflammation leads to progressive thickening, scarring, and destruction of the bile ducts. The buildup of bile, bile salts, and cholesterol in the liver causes damage to cell membranes in the liver, reduced production of bile salts, and fibrosis (development of scar tissue). Fibrosis is both a marker of liver damage and a potential contributor to liver failure. Continuing damage causes scarring or cirrhosis of the liver (the liver slowly deteriorates and malfunctions), and prevents proper liver function and impaired blood circulation in the intestines. While not bound by theory, these diseases are believed to be autoimmune diseases and the present inventor believes that modulation of a person's gut microbiota can avoid the development of such autoimmunity, thus providing a treatment and method of preventing PBC and PSC. It is believed that bacterial antigens translocate across a leaky and possibly inflamed gut wall into the portal and biliary system to induce an abnormal immune response and contribute to primary sclerosing cholangitis pathogenesis.

In various embodiments, the focus of modification of an individual's microbiome is directed to the microbiome of the small intestine, while in others it is directed to the colon, and in still others, to both. One strategy in the treatment of NAFLD is to ameliorate or turn off inflammatory triggers, with some of the main targets including cytokines such as tumor necrosis factor (TNF)-α, chemokines, TLR4, and the NLRP3 inflammasome. Gut microorganism-derived bacterial products including endotoxin (lipopolysaccharide), peptidoglycan, and bacterial DNA can travel up the portal vein to activate TLR4 and TLR9 on Kupffer cells and other hepatic cell types. In turn, this activation can lead to the release of cytokines and chemokines that promote NASH. In still other embodiments, modulation of particular bacteria by CRISPR-Cas and Cpf1 systems, for example, to address bacterial pyruvate dehydrogenase complex component E2 (PDC-E2) homologues in particular bacteria, including but not limited to *E. coli*, *Novosphingobium aromaticivorans*, *Mycobacterium* and *Lactobacillus* species, are used to effectively treat and/or prevent these diseases. There is believed to be a common core gut microbial response to chronic inflammation and immune activation, such as observed in type 2 diabetes.

In yet other embodiments of the present invention, the present inventors submit that bacterial expression of RNA molecules can be employed to generate miRNA molecules that interact with the human host mRNA during bacterial infection. Thus, such micro-RNAs derived from bacterial RNAs are used to regulate gene expression of the human host cell involved in different human diseases, including NAFLD. Bacterially derived microRNA sequences can significantly regulate the expression of various human genes and thus, enhancing an individual's gut bacteria by employing CRISPR systems to regulate microRNA sequences forms various embodiments of the present invention. In addition to NAFLD, microRNAs are believed to be involved in many human diseases, such as cancer, diabetes, rheumatoid arthritis, and others that respond to a particular bacterial environment, and thus, while the present description is focused on NAFLD, it will be understood that other diseases can similarly be addressed by employment of the systems and methods as described herein.

MicroRNAs (miRNA) are small important regulators of gene expression and are currently believed to regulate approximately 70% of human genes. More than a thousand different miRNA have been characterized in the human genome and they all are assumed to function by a similar mechanism: The miRNAs base-pair with target messenger RNA (mRNA) and recruit nucleases that degrade the targeted RNA from the termini and/or inhibit translation. In cancer and many other diseases, deregulation of gene-expression is observed and in many cases miRNAs have been shown to play an integral part or even the causative role in disease development. According to various embodiments, the present invention concerns a method for the treatment, amelioration or prevention of a disease or medical disorder associated with the presence or over-expression of microRNA. Therefore, in certain aspects of the invention, inhibiting miRNA activity is a strategy to treat disease, especially NAFLD.

miRNAs are a class of highly conserved non-coding regulatory factors that negatively regulate more than half of the protein-coding genes in mammals, are essential to most biological processes, including proliferation, differentiation and apoptosis, and their transcription is tightly controlled. In certain embodiments, a CRISPR system and/or a modified CRISPR interference system (CRISPRi) employing inactive Cas9, may be used to reversibly prevent the expression of both monocistronic miRNAs and polycistronic miRNA clusters. Such CRISPR-based systems are reversible and thus provide advantages over more conventional knockdown techniques. The CRISPR/CRISPRi system may be adapted to target a particular miRNA sequence by employing a single repression vector, often entailing using a 20-bp sequence and thus, such a CRISPR/CRISPRi method is useful in the generation of vectors that target multiple miRNAs and with reduced toxicity and can silence miRNAs with no off-target effects. Using such CRISPR systems to silence miRNAs involved in the progression of NAFLD is therefore one focus of particular embodiments of the present invention.

In various embodiments, particular bacterial species are targeted for modification and use to address the treatment of NAFLD. For example, *L. reuteri* is well-established as one of the most ubiquitous members of the naturally-occurring gut bacteria. Host-specific strains of *L. reuteri* have been documented to confer broad-spectrum protection from an assortment of microbial and chemical associated disease in humans and animals. However, traditional probiotic therapy involves administration of bacteria with the hope that some bacteria will survive the harsh gastric conditions and colonize the colon where the bacteria will reproduce and live indefinitely. Far fewer bacteria survive in the duodenum, jejunum or ileum because of factors such as acidity, immune response and bile concentration. In certain embodiments, it is believed that bacteria must be present in the duodenum or jejunum of the small intestine for lowering cholesterol and in particular bile acid. Thus, certain aspects of the present invention are directed to the modification of particular bacteria using CRISPR-Cas and/or Cpf1 systems to provide bacteria having the ability to survive the conditions in the duodenum or jejunum of the small intestine. Thus, in one embodiment, CRISPR systems are employed to render certain bacteria adaptive to harsh acid conditions and that are otherwise considered to be beneficial to a person in avoiding fatty liver disease. Highly bile salt hydrolase active bacteria provide an improved agent for reducing serum cholesterol, serum lipids, body fat, and atherogenic index and for prophylaxis and treatment of atherosclerosis, cardiovascular and cerebrovascular diseases. Modification of an individual's gut microbes to render a significant population thereof to have enhanced degrees of BSH characteristics is one objective of various embodiments of the present invention.

*Lactobacillus reuteri* (*L. reuteri*) is a well-studied probiotic bacterium that can colonize a large number of mammals. In humans, *L. reuteri* is found in different body sites, including the gastrointestinal tract, urinary tract, skin, and breast milk. Endogenous oxytocin levels are upregulated after consuming the probiotic *Lactobacillus reuteri* derived from human breast milk. The abundance of *L. reuteri* varies among different individuals. Several beneficial effects of *L. reuteri* have been noted. First, *L. reuteri* can produce antimicrobial molecules, such as organic acids, ethanol, and reuterin. Due to its antimicrobial activity, *L. reuteri* is able to inhibit the colonization of pathogenic microbes and remodel the commensal microbiota composition in the host. Second, *L. reuteri* can benefit the host immune system. For instance, some *L. reuteri* strains can reduce the production of pro-inflammatory cytokines while promoting regulatory T cell development and function. Third, bearing the ability to strengthen the intestinal barrier, the colonization of *L. reuteri* may decrease the microbial translocation from the gut lumen to the tissues. Microbial translocation across the intestinal epithelium has been hypothesized as an initiator of inflammation. Therefore, inflammatory diseases, including those located in the gut as well as in remote tissues, may be ameliorated by increasing the colonization of *L. reuteri*. Notably, the decrease in the abundance of *L. reuteri* in humans in the past decades is correlated with an increase in the incidences of inflammatory diseases over the same period of time. Direct supplementation or prebiotic modulation of *L. reuteri* may be an attractive preventive and/or therapeutic avenue against inflammatory diseases.

With the guidance provided herein, as well as the numerous references incorporated by reference herein, one of skill in the art will understand the feasibility of using engineered bacteria to directly manipulate the functional output of the microbiota without major modulation of the microbiota population and composition. Components in the normal diet and/or employing prebiotics and engineered probiotics are therefore harnessed to render a targeted effect on the host through modulating the functional output of the microbiome.

Oral administration of probiotics has been shown to significantly reduce cholesterol levels, such cholesterol-lowering effects ascribed to BSH activity. Deconjugated bile salts are less efficiently reabsorbed than their conjugated counterparts, which results in the excretion of larger amounts of free bile acids in feces. Also, free bile salts are less efficient in the solubilization and absorption of lipids in the gut. Therefore, deconjugation of bile salts is believed to lead to a reduction in serum cholesterol either by increasing the demand for cholesterol for de novo synthesis of bile acids to replace those lost in feces or by reducing cholesterol solubility and thereby absorption of cholesterol through the intestinal lumen. Microbial BSHs function in the detoxification of bile salts and in doing so increase the intestinal survival and persistence of producing strains. Thus, one embodiment of the present invention is directed to enhancing the BSH activity by a probiotic bacterium to maximize its prospects of survival in the hostile environment of the gastrointestinal tract. Increased intestinal survival increases the overall beneficial effects associated with strains possessing such BSH enhanced activities. Enhanced BSH activity benefits probiotic bacterium that are able to survive and perform in the intestinal milieu. BSH significantly contributes to bile tolerance and survival and persistence of strains in the intestinal tract. Thus, certain embodiments are directed to the manipulation of bacterial strains to enhance the BSH activity of probiotic strains (either to over express a native BSH or to express or over express a heterologous BSH) to improve their survivability in the intestinal tract. Extraction of fecal bacteria form a person and employing the techniques as described herein on such native populations to enhance various aspects thereof, including for example BSH activity, and then returning such modified gut bacteria to the individual, is one method that may be used to address NAFLD in a positive manner.

This is accomplished in various embodiments by the employment of CRISPR-Cas and Cpf1 systems to insert BSH genes in select bacteria. Certain embodiments include the administration of bile-hydrolyzing strains (especially those modified by CRISPR-Cas and/or Cpf1 systems) to control serum cholesterol. The ingestion of probiotics as described herein is believed to be deemed preferable to statins as a way to achieve a cholesterol-lowering therapy. Manipulation of BSH activity as described herein provides for more robust probiotics (whether delivered orally or via the fecal transplantations as described herein) with improved competitiveness and performance. Statin drugs target many of the underlying inflammatory pathways involved in metabolic syndrome (MetS). Thus, certain embodiments relate to the use of CRISPR-Cas systems to modify bacteria of an individual's microbiome so that they produce effective levels of statin drugs. The metabolic syndrome (MetS) is comprised of a cluster of closely related risk factors, including visceral adiposity, insulin resistance, hypertension, high triglyceride, and low high-density lipoprotein cholesterol; all of which increase the risk for the development of type 2 diabetes and cardiovascular disease. A chronic state of inflammation appears to be a central mechanism underlying the pathophysiology of insulin resistance and MetS. Thus in various embodiments of the present invention, use of probiotics and prebiotics in combination, as described herein, is employed to address the cause of NAFLD, but that is also believed to address related conditions, such as MetS.

In one embodiment, the bacteria employed and that are modified via CRISPR-Cas and Cpf1 to enhance expression of BSH include *Lactobacillus, Bifidobacteria, Pediococcus, Streptococcus, Enterococcus,* or *Leuconostoc*. In another embodiment, the *Lactobacillus* is *Lactobacillus reuteri*, optionally, *Lactobacillus reuteri* (NCIMB 701359), *Lactobacillus reuteri* (NCIMB 701089), *Lactobacillus reuteri* (ATCC 55148), *Lactobacillus reuteri* (ATCC 23272), *Lactobacillus reuteri* (NCIMB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144). In another embodiment, the *Lactobacillus reuteri* adheres to the gastrointestinal epithelial cells, competes for adhesion, or inhibits the binding of other bacteria due to cell surface proteins.

The human gut is a rich habitat populated by numerous microorganisms, each having a CRISPR system. In certain embodiments, the CRISPR-Cas system may be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference. Another aspect of certain embodiments includes making synthetic CRISPR-containing RNAs that target genes of interest and using them with Cas enzymes.

In various embodiments, the CRISPR-Cas and or Cpf1 system is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas/Cpf1 systems. Because of the sequence specificity of targeting, CRISPR-Cas/CPF1 systems may be used to distinguish strains separated by only a few base pairs.

There are ongoing ethical concerns arising with respect to the use of CRISPR-Cas systems—especially as it relates to modification of the human genome. In preferred embodiments of the present invention, however, such issues are much less prevalent for various reasons. First, because preferred embodiments relate to the modification of microbes—rather than to the human genome—and especially those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Modifying the human genome, made possible by the CRISPR technique, has its upsides but also equally daunting downsides. Permanent deletion of genes from the human genome is much more controversial than deletion or modification of bacterial genes. Thus, one desirable aspect of the present invention is directed to the far less controversial modification of gut microbes resident in the human being to promote health and to trigger the desired immune responses as described herein.

In other embodiments, the use of CRISPR-Cas systems is employed to increase butyrate production of select bacteria. For example, *F. prausnitzii*, one of the most abundant species in the colon, is an important producer of butyrate, a major product of carbohydrate fermentation which is implicated in providing protection against colorectal cancer and ulcerative colitis. CRISPR systems are used to enhance the production of butyrate by insertion of genes into select *F. prausnitzii* bacteria to protect against colorectal cancer and other diseases.

Because CRISPR-Cas/Cpf1 acts before transcription occurs, it is able to be employed to target regulatory and other elements on the DNA of microbes that make up a person's gut microbiome. In certain embodiments, CRISPR-Cas may be employed to deliver fluorescent markers to certain DNA sequences, thus permitting one to determine whether any particular sample has been treated in accordance with the present invention, thus ensuring, for example, identity of various materials, compliance with safety issues, effectiveness of gene expression or excision, etc. permitting labeling of living cells with a desired color to discern particular attributes and states.

Other embodiments are focused on diet as it relates to the use of probiotics. The gut microbiota plays a critical role in transforming dietary polyphenols into absorbable biologically active species, acting on the estimated 95% of dietary polyphenols that reach the colon. Certain embodiments rely upon the ability to deliver agents via mucosal adhesive strips, such as described, for example, in U.S. Pat. No. 8,701,671, which is fully incorporated herein by this reference. Thus, in various embodiments of the present invention, the engineering of communal bacteria with improved properties using a CRISPR/Cas system is employed to provide for the enhancement of health, especially as it relates to an individual's microbiome. In certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). In various embodiments, the delivery vehicle is a bacteriophage. Thus, various embodiments of the present invention include the use of CRISPR-Cas, with the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe DNA—rather than attempting to change or modify the DNA of a human.

The present invention is one way in which human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system.

Another aspect of the present invention includes the ability to load or impregnate mucosal strips with any number of active agents to achieve other desirable aspects, such as administration of particular vitamins, medicinal components, and certain CRISPR-Cas modified bacteria. In some embodiments the microbes are encapsulated within encapsulation structures selected to provide the desired degree of adhesion to the mucous membranes of the throat, gut, etc., and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The strips of the present invention provide the requisite pliability and tensile strength necessary to securely adhere to a person's mucosal tissues for at least one hour, more preferably at least two hours, and preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts. In certain embodiments, a mucosal adhesive strip has a coated surface for resisting bioadhesion that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. In this regard, one aspect of the present invention is directed to the modification of certain human-specific pathogens by targeting one or more virulence factors thereof, preferably by using CRISPR-Cas or CRISPR-Cpf1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. Certain embodiments provide for the delivery, via the strips as described herein, of one or more of the following microorganisms selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum,* and *Lactobacillus ingluviei*. The CRISPR-Cas system is preferably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus* fermen turn, *Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Microorganisms for the purpose of patent deposition. In a preferred embodiment of the invention, strips containing effective amounts of these bacteria are provided that are attached to the soft palate region of a person's mouth or on other mucosal surfaces. Other LAB that may be employed in various embodiments include the following: *lactobacillus slaivarius* CICC 23174; *Lactobacillus plantarum* CGMCC 1.557, *Lactobacillus rhamnosus* ATCC 53103, and *Lactobacillus acidophilus* ATCC 4356.

Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a particular bacteria in a person's gut from being able to effectively attach to epithelial tissue; or alternatively, to coaggregate with other bacteria.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 20040136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg; 20150064138 to Lu; 20150329875 to Gregory; 20150329555 to Liras; 20080267933 to Ohlson et. al.; 20120058094 to Blasser et. al.; U.S. Pat. No. 8,716,327 to Zhao; 20110217368 to Prakash et. al.; 20140044734 to Sverdlov et al.

In addition to the above, to comply with written description and enablement requirements, all references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: 20170079947 to Richards; 20140296139 to Cohen et al.; 20160175327 to Adams et. al.; 20100081681 to Blagosklonny and 20120283269 to Blagosklonny; U.S. Patent Publication Nos. 20140030332 to Baron, et al., 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; U.S. Pat. No. 9,044,420 to Dubensky, Jr et al.; 20160120915 to Blaser et. al.; 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 201/

50132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. Nos. 6,287,610, 6,569,474, U.S. 2002/0009520, U.S. 2003/0206995, U.S. 2007/0054008; and U.S. Pat. No. 8,349,313 to Smith; U.S. Pat. No. 9,011,834 to McKenzie; 20150004130 to Faber et. al, 20160206666 to Falb; 20160206668 to Kort et al; and WO2015069682A2 to Asesvelt, et. al.; 20160199424 to Berry et al.; 20130326645 to Cost et al.; 2012/0276149 to Littman; U.S. Pat. No. 9,314,489 to Kelly et al.; U.S. Pat. Publication No. 2016/0024510 to Bikard et al.; U.S. Pat. Publication No. 2018/0015131 to Gajew.; U.S. Pat. No. 8,815,538 to Lanzalaco, et al.; 20150374607 to Lanzalaco, et al.; 20150361436 to Hitchcock et al.; 20150353901 to Liu et al.; U.S. Pat. No. 5,518,733 to Lamothe, et al.; 20150259728 to Cutcliffe et al. U.S. Pat. No. 8,685,389 to Baur; 20140065209 to Putaala et al.; U.S. Pat. No. 8,481,299 to Gueniche; WO 2011029701 to Banowski; 20150071957 to Kelly; 20150017227 to Kim; U.S. Pat. No. 7,820,420 to Whitlock; 20150202136 to Lanzalaco et al.; U.S. Pat. No. 5,518,733 to Lamothe, et al.; U.S. Pat. No. 8,951,775 to Castiel; WO 2006/07922; U.S. Pat. No. 9,234,204 to Qvit-Raz et al.; U.S. Pat. No. 8,758,764 to Masignani, et al.; U.S. Pat. No. 9,028,841 to Henn et al.; 20160008412 to Putaala et al., 20150064138 to Lu; 20150017227 to Kim; United States Patent Application No. 20160314281 to Apte; 20160151427 to Whitlock et al.; 20140044677 to Raz et al.; 20160168594 to Zhang et al. U.S. Pat. Nos. 7,267,975; 9,288,981; United States Patent Application No. 20160122806; U.S. Pat. No. 9,234,204 to Noga Qvit-Raz; US20120301452; 20160271189 to Cutcliffe; US Pat. Applic. No. 2008242543; 20160040216 to Wilder; and United States Patent Application No. 20160089315 to Kleinberg, et al., 20070148136 to Whitlock et al., 20190059314 to Aharoni; 20200009268 to Scholz and 20200009185 to Shin; US Pat. Publication No. 20190388471 to June; 20190000815 to Melin; 20180258100 to Gregory; 20170027914 to Qi; 20130310416 to Blagosklonny.

Another aspect of certain embodiments of the present invention is directed to a thin film mucosal layered strip wherein modified bacteria (e.g via the CRISPR-Cas system) is encapsulated in a frangible enclosure and is present in an amount of at least about 0.5 ml. Other treatment agents may be encapsulated in such strips, such that antibiotics or co aggregation agents or LAB, etc. can be encapsulated in a manner that they can be released at a time when the person so desires and/or when the strip dissolves to a certain extent, e.g. when the walls of the encapsulating shell is worn thin enough to fracture to release the agent(s). The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on a particular mucosal surface, such as on the soft palette of a human, such that the person's tongue, when pressing against such capsule, can cause it to fracture to release the contents of the capsule. In other embodiments, two or more different materials may be released.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

The invention claimed is:

1. A method for reducing the likelihood of developing non-alcoholic fatty liver disease, comprising: providing to an individual a population of beneficial bacteria selected from the group consisting of *Lactobacillus* species; administering at least 6 grams per day of fiber to the individual to maintain a therapeutically effective amount of the beneficial bacteria in the gut of the individual; and inhibiting monoacylglycerolacyltransferase-3 (MGAT3) synthesis in the individual to lower triacylglycerol (TAG) production.

2. The method as set forth in claim 1, wherein the beneficial bacteria are encapsulated in a frangible enclosure.

3. The method as set forth in claim 1, further comprising inhibiting expression of diacylglycerolacyltransferase-2 (DGAT-2) in said individual.

4. The method as set forth in claim 1, further comprising increasing the levels of *Roseburia* in the individual's gut microbiome.

5. The method as set forth in claim 4, further comprising increasing the populations of at least two of the following in the individual's gut microbiome: *Akkermansia muciniphila, Faecalibacterium prausnitzii, Bifidobacterium longum, Roseburia intestinalis*.

6. A method for reducing the likelihood of non-alcoholic fatty liver disease, comprising: providing to an individual a population of beneficial bacteria selected from the group consisting of *Lactobacillus* species; administering at least 6 grams per day of fiber to the individual to maintain a therapeutically effective amount of the beneficial bacteria in the gut of the individual; inhibiting expression of diacylglycerolacyltransferase-2 (DGAT-2) in said individual; and increasing the levels of *Roseburia* in the individual's gut microbiome.

7. The method as set forth in claim 6, further comprising increasing the populations of at least two of the following in the individual's gut microbiome: *Akkermansia muciniphila, Faecalibacterium prausnitzii, Bifidobacterium longum, Roseburia intestinalis, Coprococcus* spp. and *Veillonella*.

8. The method as set forth in claim 6, wherein the beneficial bacteria are encapsulated in a frangible enclosure.

9. The method as set forth in claim 6, wherein the population of beneficial bacteria include bacteria that have been modified using a clustered regularly interspaced short palindromic repeats (CRIPSR)-CRISPR associated protein (Cas) system or a CRISPR from *Prevotella* and Franscisella 1 (Cpf1a) system.

10. The method as set forth in claim 6, further comprising inhibiting monoacylglycerolacyltransferase-3 (MGAT3) synthesis in the individual to lower triacylglycerol (TAG) production.

11. A method for reducing the likelihood of developing non-alcoholic fatty liver disease, comprising: providing to an individual a population of beneficial bacteria selected from the group consisting of *Lactobacillus* species; administering at least 6 grams per day of fiber to the individual to maintain a therapeutically effective amount of the beneficial bacteria in the gut of the individual; and increasing the levels of at least two bacteria selected from the group consisting of *Akkermansia muciniphila, Faecalibacterium prausnitzii, Bifidobacterium longum, Roseburia intestinalis*, and *Coprococcus* in the individual's gut microbiome.

12. The method as set forth in claim 11, wherein the beneficial bacteria are encapsulated in a frangible enclosure.

13. The method as set forth in claim 11, further comprising inhibiting expression of diacylglycerolacyltransferase-2 (DGAT-2) in said individual.

14. The method as set forth in claim 11, further comprising inhibiting monoacylglycerolacyltransferase-3 (MGAT3) synthesis in the individual to lower triacylglycerol (TAG) production.

15. The method as set forth in claim 11, wherein a secretion of glucagon-like peptide-1 (GLP-1) is stimulated in the individual due to the production of butyrate by the administration of the at least two bacteria.

16. A method for reducing the likelihood of developing non-alcoholic fatty liver disease, comprising: providing to an individual through oral administration a population of beneficial bacteria that comprises bacteria selected from the group consisting of *Akkermansia muciniphila, Faecalibacterium prausnitzii, Bifidobacterium longum, Roseburia intestinalis, Coprococcus* spp. and *Veillonella*, wherein a secretion of glucagon-like peptide-1 (GLP-1) is stimulated in the individual due to the production of butyrate by the beneficial bacteria; wherein the beneficial bacteria are encapsulated in a frangible enclosure.

17. A method for reducing the likelihood of developing non-alcoholic fatty liver disease, comprising: providing to an individual through oral administration a population of beneficial bacteria that comprises bacteria selected from the group consisting of *Akkermansia muciniphila, Faecalibacterium prausnitzii, Bifidobacterium longum, Roseburia intestinalis, Coprococcus* spp. and *Veillonella*, wherein a secretion of glucagon-like peptide-1 (GLP-1) is stimulated in the individual due to the production of butyrate by the beneficial bacteria; further comprising inhibiting expression of diacylglycerolacyltransferase-2 (DGAT-2) in said individual.

18. A method for reducing the likelihood of developing non-alcoholic fatty liver disease, comprising: providing to an individual through oral administration a population of beneficial bacteria that comprises bacteria selected from the group consisting of *Akkermansia muciniphila, Faecalibacterium prausnitzii, Bifidobacterium longum, Roseburia intestinalis, Coprococcus* spp. and *Veillonella*, wherein a secretion of glucagon-like peptide-1 (GLP-1) is stimulated in the individual due to the production of butyrate by the beneficial bacteria; further comprising inhibiting monoacylglycerolacyltransferase-3 (MGAT3) synthesis in the individual to lower triacylglycerol (TAG) production.

\* \* \* \* \*